US010639186B2

(12) United States Patent
Santin et al.

(10) Patent No.: US 10,639,186 B2
(45) Date of Patent: *May 5, 2020

(54) NASAL CONGESTION, OBSTRUCTION RELIEF, AND DRUG DELIVERY

(71) Applicant: SANOSTEC CORP, Beverly Farms, MA (US)

(72) Inventors: Ernest Santin, Beverly, MA (US); Louise S. MacDonald, Beverly, MA (US); Scott D. MacDonald, Beverly, MA (US)

(73) Assignee: SANOSTEC CORP., Beverly Farms, MA (US)

( * ) Notice: Subject to any disclaimer, the term of this patent is extended or adjusted under 35 U.S.C. 154(b) by 172 days.

This patent is subject to a terminal disclaimer.

(21) Appl. No.: 15/361,647

(22) Filed: Nov. 28, 2016

(65) Prior Publication Data

US 2017/0071777 A1    Mar. 16, 2017

Related U.S. Application Data

(63) Continuation of application No. 13/848,374, filed on Mar. 21, 2013, now Pat. No. 9,504,599, which is a
(Continued)

(51) Int. Cl.
*A61F 5/08*    (2006.01)
*A61M 15/08*   (2006.01)
(Continued)

(52) U.S. Cl.
CPC .............. *A61F 5/08* (2013.01); *A61F 5/56* (2013.01); *A61M 15/08* (2013.01);
(Continued)

(58) Field of Classification Search
CPC ..... A61M 16/0666–0677; A61M 29/00; A61F 5/08; A62B 23/00; A62B 23/06;
(Continued)

(56) References Cited

U.S. PATENT DOCUMENTS

| 682,123 A | 9/1901 | Wilson |
| 753,133 A | 2/1904 | Gamble |

(Continued)

FOREIGN PATENT DOCUMENTS

| DE | 199 03 782 C1 | 7/2000 |
| DE | 10 2005 037 843 A1 | 2/2007 |

(Continued)

OTHER PUBLICATIONS

**Egan , K. et al., "A Novel Intranasal Stent for Functional Rhinoplasty and Nostril Stenosis," Laryngoscope 115 (5):903-09 (May 2005).

(Continued)

*Primary Examiner* — Jonathan A Hollm
(74) *Attorney, Agent, or Firm* — Nutter McClennen & Fish LLP

(57) ABSTRACT

A nasal insert may include a wall in the shape of a tube, the wall including a first end defining a first orifice and a second end defining a second orifice. The first end may have a diameter, diagonal measurement, or cross-sectional area larger than that of the second end. The first end may define at least one break in the wall, so that the first end incompletely encircles the first orifice. The second end may completely encircle the second orifice.

18 Claims, 25 Drawing Sheets

Related U.S. Application Data continuation of application No. 11/290,047, filed on Nov. 30, 2005, now Pat. No. 8,403,954, which is a continuation-in-part of application No. 10/842,220, filed on May 10, 2004, now Pat. No. 9,474,642, which is a continuation-in-part of application No. 10/434,669, filed on May 9, 2003, now Pat. No. 7,390,331, which is a continuation-in-part of application No. 09/862,966, filed on May 22, 2001, now Pat. No. 6,562,057.

(51) Int. Cl.
| | | |
|---|---|---|
| A61M 16/06 | (2006.01) | |
| A61M 29/00 | (2006.01) | |
| A61M 31/00 | (2006.01) | |
| A61M 16/10 | (2006.01) | |
| A62B 23/06 | (2006.01) | |
| A61F 5/56 | (2006.01) | |

(52) U.S. Cl.
CPC ...... *A61M 15/085* (2014.02); *A61M 16/0666* (2013.01); *A61M 16/105* (2013.01); *A61M 16/106* (2014.02); *A61M 29/00* (2013.01); *A61M 31/00* (2013.01); *A62B 23/06* (2013.01)

(58) Field of Classification Search
CPC ........ A61B 17/12022; A61B 17/12104; A61B 17/24; A61B 2017/246–248
See application file for complete search history.

(56) References Cited

U.S. PATENT DOCUMENTS

| | | |
|---|---|---|
| 810,617 A | 1/1906 | Carence |
| 878,223 A | 2/1908 | Meisselbach |
| 888,869 A | 5/1908 | Clark |
| 1,034,123 A | 7/1912 | Knowlson |
| 1,077,574 A | 11/1913 | Woodward |
| 1,087,186 A | 2/1914 | Scholfield |
| 1,139,357 A | 5/1915 | Garske |
| 1,160,797 A | 11/1915 | Wallin |
| 1,256,188 A | 2/1918 | Wilson |
| 1,311,461 A | 7/1919 | Reynard |
| 1,322,375 A | 11/1919 | Un |
| 1,481,581 A | 1/1924 | Woodward |
| 1,839,606 A | 1/1932 | Simmons |
| 2,010,485 A | 8/1935 | Heath |
| 2,151,227 A | 3/1939 | Pawelek |
| 2,237,954 A | 4/1941 | Wilson |
| 2,264,153 A | 11/1941 | Bowe |
| 2,277,390 A | 3/1942 | Crespo |
| 2,335,936 A | 12/1943 | Hanlon |
| 2,433,565 A | 12/1947 | Korman |
| 2,515,756 A | 7/1950 | Bove |
| 2,569,743 A | 10/1951 | Carlock |
| 2,663,297 A | 12/1953 | Turnberg |
| 2,672,138 A | 3/1954 | Carlock |
| 2,890,695 A * | 6/1959 | Safstrom ............... A62B 23/06 128/206.11 |
| 3,424,152 A | 1/1969 | Kuhlman |
| 3,463,149 A | 8/1969 | Albu |
| 3,710,799 A | 1/1973 | Caballero |
| 3,742,943 A | 7/1973 | Malmin |
| 3,747,597 A | 7/1973 | Olivera |
| 3,802,426 A | 4/1974 | Sakamoto |
| 4,105,035 A | 8/1978 | Rella |
| 4,120,299 A | 10/1978 | Russo |
| 4,221,217 A | 9/1980 | Amezcua |
| 4,267,831 A | 5/1981 | Aguilar |
| 4,414,977 A | 11/1983 | Rezakhany |
| D279,708 S | 7/1985 | Child |
| 4,573,461 A | 3/1986 | Lake |
| 4,592,357 A | 6/1986 | Ersek |
| 5,417,205 A | 5/1995 | Wang |
| 5,425,359 A | 6/1995 | Liou |
| 5,479,944 A | 1/1996 | Petruson |
| 5,533,503 A | 7/1996 | Doubek et al. |
| 5,601,594 A | 2/1997 | Best |
| 5,603,317 A | 2/1997 | Farmer |
| 5,665,104 A | 9/1997 | Lee |
| 5,725,547 A | 3/1998 | Chuter |
| 5,775,335 A | 7/1998 | Seal |
| 5,816,241 A | 10/1998 | Cook |
| 5,853,422 A | 12/1998 | Huebsch et al. |
| 5,895,409 A | 4/1999 | Mehdizadeh |
| 5,925,060 A | 7/1999 | Forber |
| 5,931,852 A | 8/1999 | Brennan |
| 5,941,244 A | 8/1999 | Yamazaki et al. |
| 6,004,342 A | 12/1999 | Filis |
| 6,017,315 A | 1/2000 | Starr et al. |
| 6,024,756 A | 2/2000 | Huebsch et al. |
| 6,106,541 A | 8/2000 | Hurbis |
| 6,386,197 B1 | 5/2002 | Miller |
| 6,416,540 B1 | 7/2002 | Mathur |
| 6,561,188 B1 | 5/2003 | Ellis |
| 6,562,057 B2 | 5/2003 | Santin |
| 6,602,282 B1 | 8/2003 | Yan |
| 6,863,066 B2 | 3/2005 | Ogle |
| 6,893,450 B2 | 5/2005 | Foster |
| 6,978,781 B1 | 12/2005 | Jordan |
| 7,331,989 B2 | 2/2008 | Houston et al. |
| 7,390,331 B2 | 6/2008 | Santin et al. |
| 7,582,111 B2 | 9/2009 | Krolik et al. |
| 7,637,939 B2 | 12/2009 | Tischler |
| 7,856,979 B2 | 12/2010 | Doshi et al. |
| 8,262,688 B2 | 9/2012 | Santin et al. |
| 8,403,954 B2 | 3/2013 | Santin et al. |
| 9,242,080 B2 | 1/2016 | MacDonald |
| 9,474,642 B2 | 10/2016 | Santin et al. |
| 9,504,599 B2 | 11/2016 | Santin et al. |
| 2003/0079749 A1 | 5/2003 | Strickland et al. |
| 2003/0106555 A1 | 6/2003 | Tovey |
| 2003/0195552 A1 | 10/2003 | Santin |
| 2004/0147954 A1 | 7/2004 | Wood |
| 2005/0021073 A1 | 1/2005 | Santin et al. |
| 2006/0085027 A1 | 4/2006 | Santin et al. |
| 2006/0150978 A1 | 7/2006 | Doshi et al. |
| 2006/0259064 A1 | 11/2006 | Maryanka |
| 2007/0010851 A1 | 1/2007 | Chanduszko et al. |
| 2007/0066198 A1 | 3/2007 | Rambosek et al. |
| 2007/0106328 A1 | 5/2007 | Wardle et al. |
| 2007/0208368 A1 | 9/2007 | Katoh et al. |
| 2007/0239199 A1 | 10/2007 | Jayaraman |
| 2008/0183299 A1 | 7/2008 | Monga et al. |
| 2008/0262531 A1 | 10/2008 | Santin et al. |
| 2009/0093840 A1 | 4/2009 | MacDonald |
| 2010/0063532 A1 | 3/2010 | Moore |
| 2012/0283769 A1 | 11/2012 | Cruise et al. |
| 2013/0109987 A1 | 5/2013 | Kunis et al. |
| 2013/0131716 A1 | 5/2013 | Cruise et al. |
| 2013/0296809 A1 | 11/2013 | Santin et al. |
| 2016/0206468 A1 | 7/2016 | MacDonald |
| 2017/0100275 A1 | 4/2017 | Santin et al. |

FOREIGN PATENT DOCUMENTS

| | | |
|---|---|---|
| GB | 0 210 982 A | 2/1924 |
| GB | 2 126 101 A | 3/1984 |
| JP | 11-192251 A | 7/1999 |
| JP | 2002-301152 A | 10/2002 |
| WO | 2004/026391 A1 | 4/2004 |
| WO | 2004/069110 A1 | 8/2004 |
| WO | 2007/018458 A1 | 2/2007 |

OTHER PUBLICATIONS

\*\*European Search Report and Supplementary Search Report, for EP06840036.5, dated Oct. 27, 2009 and Nov. 4, 2009.
\*\*Extended European Search Report for Application No. 08835440.2 dated Jun. 26, 2013 (6 pages).

(56) References Cited

OTHER PUBLICATIONS

\*\*Indian Office Action for Application No. 3358/CHENP/2008, dated Aug. 26, 2016 (7 pages).
\*\*International Search Report, for PCT/US04/014501, dated Nov. 23, 2004.
\*\*International Search Report, for PCT/US06/61280, dated Jul. 17, 2008.
\*\*International Search Report, for PCT/US08/078781, dated Mar. 16, 2009.
\*\*Japanese Office Action dated Mar. 5, 2013 for Application 2010-528169 (3 Pages).
\*\*Japanese Office Action dated Apr. 19, 2016 for Application 2010-528169, Appeal No. 2015-000864 (11 pages).

\* cited by examiner

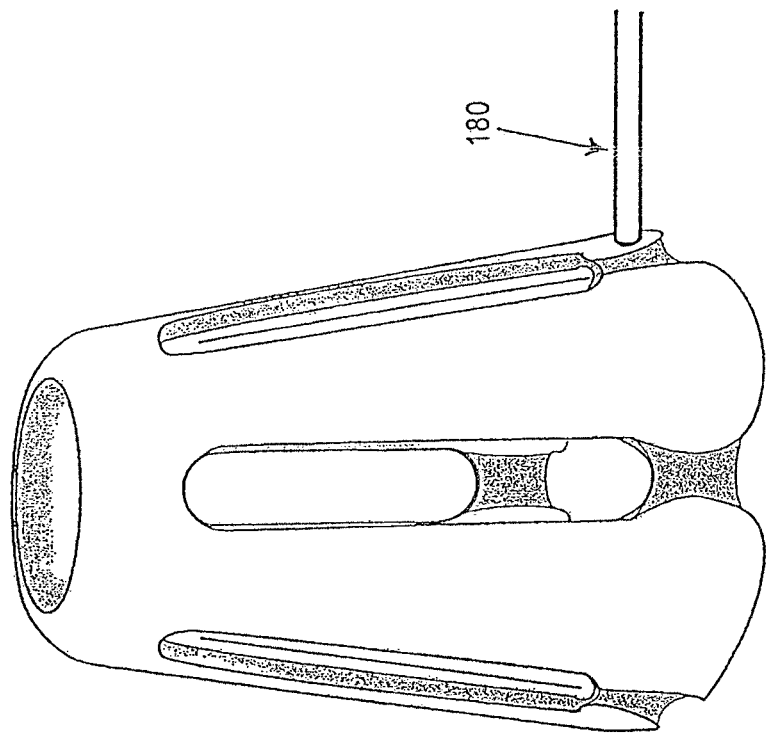
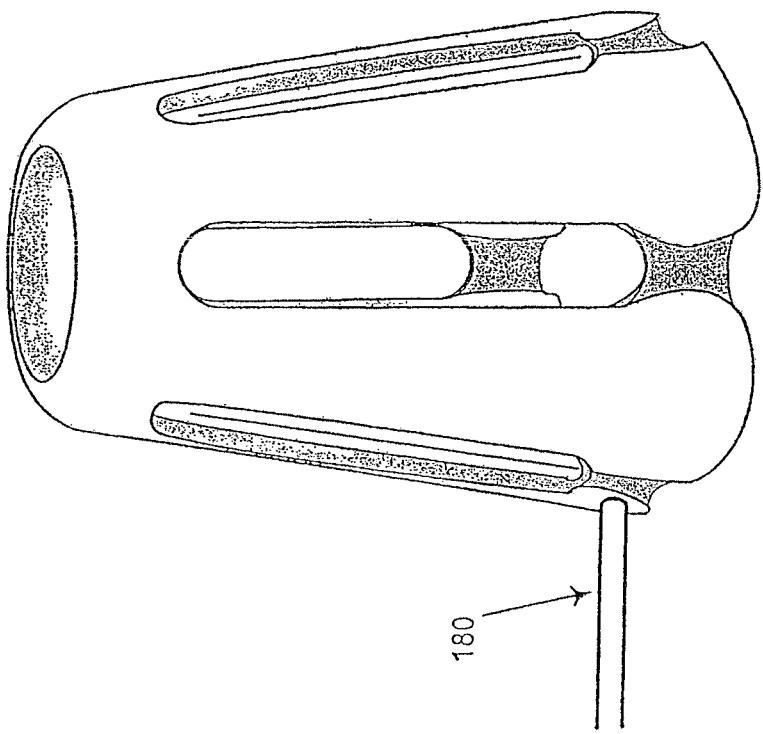
Fig. 21

NASAL CONGESTION, OBSTRUCTION RELIEF, AND DRUG DELIVERY

CROSS-REFERENCE TO RELATED APPLICATIONS

This application is a continuation of Ser. No. 13/848,374, filed Mar. 21, 2013, which is a continuation of Ser. No. 11/290,047, filed Nov. 30, 2005, now U.S. Pat. No. 8,403, 954, which is a continuation-in-part of U.S. patent application Ser. No. 10/842,220, filed May 10, 2004, now U.S. Pat. No. 9,474,642, which is a continuation-in-part of U.S. patent application Ser. No. 10/434,669, filed May 9, 2003, now U.S. Pat. No. 7,390,331, which is a continuation-in-part of U.S. patent application Ser. No. 09/862,966, filed May 22, 2001, now U.S. Pat. No. 6,562,057, the disclosures of each of which are hereby incorporated herein by reference.

FIELD

This disclosure pertains to methods and devices for nasal congestion, obstruction relief, and nasal drug delivery, and in particular to methods and devices for improving nasal breathing, treatment of sinus conditions, and reducing snoring.

BACKGROUND

Nasal obstruction is characterized by anatomical conditions including nasal valve collapse, nasal valve obstruction, septal deviation, and medium hypertrophy. These conditions obstruct and restrict nasal airflow causing difficulties in breathing through the nose.

Limited or obstructed nasal airflow reduces the normal ventilation of sinuses. Properly ventilated sinuses allow healthy draining for cleaning of the sinuses. Without proper ventilation, sinuses may not drain properly, which can cause infections in the sinuses. Chronic sinusitis is a condition characterized by long lasting sinus infections, which are caused by obstructed or restricted nasal airflow.

Snoring is a condition characterized by rough, loud, rattling breathing, or aspiratory noise in the throat during sleep or deep coma. The characteristic snoring noise is produced by vibration of the soft palate (the soft tissue in the roof of the mouth near the throat) or vocal chords by inhaled or exhaled air. As the soft palate vibrates, the lips, cheeks, and nostrils may also vibrate, making the snoring louder.

Snoring can be caused by underlying physical or disease conditions that restrict air passages and force the patient to breathe through their mouth with exaggerated force to move air through narrowed nasal passages. Chronic snoring can be the result of obstruction of nasal airways, septal deviation, or obstructed nasal passages. Temporary snoring, or a sudden onset of snoring can be the result of congestion or swollen nasal mucus membranes, as with a cold or hay fever, or a nasal polyp.

Anatomical deformities in the airway such as septal deviation, medium hypertrophy, obstructed nasal valves and nasal valve collapse can diminish the airway size. Fat deposits around the nasal passages, as found in obesity, can make the nasal passages smaller. Poor muscle tone in the muscles of the tongue and throat, or medications and foods (such as alcohol) that relax these muscles also increase snoring.

Snoring can cause relationship problems between partners, and lead to a loss of intimacy and deterioration of relationships. Loss of sleep, or insufficient rest during sleep increases irritability, reduces memory and concentration, and decreases work performance.

A number of methods and devices have been developed to reduce or eliminate snoring. Some devices are external to the patient and include buzzer systems and alarms that wake the patient. Special pillows, neck collars, chin braces and head straps have also been tested in an effort to control snoring. When nasal obstruction, chronic sinusitis, or snoring is caused by serious deformity, surgery has been performed to remove anatomical obstructions, such as removing tonsils, or correcting medium hypertrophy, or septal deviation. For snoring, occasionally a procedure called UPPP (Uvulopalatopharyngoplasty) is recommended. This procedure acts like an internal facelift, tightening loose tissue. However, the success rate is only 50%. Laser surgery to correct airway defects is also available in some cases.

Other remedies for chronic sinusitis or snoring include prescription antibiotics, herbal and homeopathic rinses, sprays or portions, and OTC medications such as decongestants and anti-histamines. Diet and lifestyle changes may reduce snoring to some degree. Nasal valve collapse is a soft tissue condition that is inoperable. Remedies are limited to rigid and metal spring like products. Use of these type of products is limited due to the discomfort or metal taste.

Various devices have been developed for nasal congestion and obstruction relief and sinus or snore relief that keep the mouth, or nasal passages open, or the tongue depressed. Devices marketed for snoring through the dental channel can be expensive custom-fit, or inexpensive over the counter mouth pieces. Adhesive nasal strips, which are applied externally to either side of the nose, have been developed. While these strips may dilate the nasal passages to small degree, they do not work well in patients with significant anatomical deformities or obstructions in the nose. Air masks that force pressurized air into the mouth and lungs are available. These devices can be cumbersome, unsightly, painful, or expensive, and the patient may abandon these approaches in short time.

Sinusitis is another common nasal disease. Sinusitis is inflammation or infection of the mucous membranes that line the inside of the nose and sinuses. It can be caused by bacteria, viruses, and possibly by allergies. Chronic sinusitis is a prolonged sinus infection which generally last longer than 12 weeks. Chronic sinusitis is difficult to treat because it responds slowly to medications. Conventional treatment for chronic sinusitis includes oral antibiotics, nasal spray, and sinus surgery. These treatments generally cannot get directly to the source of the problem, or they may cause undesirable side effects.

SUMMARY

The disclosed devices and methods may be used to increase airflow through the nasal passages. Such increase can help reduce or eliminate a wide variety of nasal, sinus, and upper airway disorders, including snoring, sleep apnea, nasal congestion, and nasal obstruction. The disclosed devices and methods may also be used to treat chronic sinusitis, rhinitis, and allergies.

In one embodiment, a nasal insert may include a wall in the shape of a tube, the wall including a first end defining a first orifice and a second end defining a second orifice. The first end may have a diameter, diagonal measurement, or cross-sectional area larger than that of the second end. The first end may define at least one break in the wall, so that the first end incompletely encircles the first orifice. The second end may completely encircle the second orifice.

In another embodiment, a nasal insert may include a wall in the shape of a tube, the wall including a first end defining a first orifice and a second end defining a second orifice. The first end may have a diameter, diagonal measurement, or cross-sectional area larger than that of the second end. The first end may include at least one thinned or webbed portion that is more flexible that the rest of the first end. The second end may completely encircle the second orifice.

In another embodiment, a "dual tube" nasal breathing assist devices may have a pair of open-ended tubular elements connected together by a coupler element. The tubular elements are preferably conic-frustum shaped along a tube axis, having a relatively large first end and a relatively smaller second end, and tapering from the first end to the second end along the tube axis. In some embodiments, each tubular element may have passageways extending through the tubular elements transverse to the tube axis. These passageways may be elongated, and extend at least in part in the direction of the tube axes.

The coupler element maintains the tubular elements in a generally parallel relationship to each other in a common plane and in a spaced-apart relation which corresponds generally to the separation between the user's nostrils.

In one embodiment, the coupler element is a resilient, nominally curved strut lying in a plane substantially perpendicular to the tube axes, permitting relative angular motion of the tube elements about an axis perpendicular to the tube axes.

In an alternate embodiment, the coupler element is a resilient, nominally curved strut lying in a plane substantially parallel to the tube axes, permitting relative angular motion of the tube element about an axis parallel to the tube axes.

In another embodiment of the invention, a "single tube" nasal breathing assist device is a single, open-ended, resilient tubular element, adapted for insertion into a user's nostril. The tubular element is conic-frustum shaped, having a relatively large diameter first end and a relatively smaller diameter second end, and a taper extending from the first end to the second end along a tube axis. The tubular element may have passageways extending through the tubular element transverse to the tube axis. In one form, these passageways may be elongated. The single tube may be used in a user's nostril, and if desired, together with another single tube in the user's other nostril. In this form, the tubes are not coupled to each other.

In some forms of both the single tube or dual tube embodiments of the invention, the tubular elements have a tab extending from the first (i.e. relatively large) end which extends substantially parallel to the tube axis and is elongated in the direction of the tube axis. In yet another embodiment, each tube element has a tab support extending radially from the first end in a direction substantially perpendicular to the tube axis. At least one tab extends from the tab support, and is elongated in the direction of the tube axis. The tabs may be resiliently deformable, so as to permit elastic deformation in use, providing a frictional holding force when engaging the nose. Alternatively, the tabs may be non-resiliently deformable, permitting inelastic deformation, so that a user can "pinch" the tabs so that they capture and hold the nose. The non-resilient tabs are preferably made with a stiffening material embedded in, affixed to, or of plastic or metal, for example, copper, aluminum, but may be made of other materials that may be non-resiliently deformed. The tab preferably includes at least one relatively small protrusion extending from a distal end of the tab. The distal end is distal from the first end of the tubular element. The relatively small protrusion may also extend from the outer surface of the tubular element opposing the distal end of the tab. The tab and the protrusion help to prevent the device from slipping out of a user's nose.

In another embodiment, the tab has an inner surface, which faces the tubular element and is at least partially coated with adhesive. In use, after the device is inserted into a user's nostrils, the tab and the outer surface of the tubular element hold the lateral wall of the user's nose, and the adhesive coating increases the friction between the tab and the outer surface of the user's nose, and make the tab stick to the outer surface of the user's nose, thus increasing the stability of the device within the user's nose.

The tubular element includes, preferably at its large end, an open-faced channel extending about its tube axis. The device further includes a filter having a peripheral frame contoured to snap-fit in the open-faced channel. The filter includes a filter medium, preferably but not necessarily, a composite filter of manmade or natural materials, i.e. paper, metal or plastic with or without a coating of absorbent materials, spanning the peripheral frame. In an alternate embodiment, at least one relative small protrusion extends from an inner surface of the channel. The filter is adapted to snap-fit over the protrusion into the channel and is retained by the protrusion, so that the filter cannot slip out from the channel when the device is in use. In a preferred embodiment, the protrusion extends throughout an inner circumference of the channel. In another preferred form, the filter includes a liner portion extending along a central axis between a relatively large end and a relatively small end, and a filter medium spanning at least one of the relatively large end and the relatively small end. In an alternative form, the liner portion and the filter medium are integrally constructed from a sheet or composite of a filter medium.

In another embodiment, the device is embedded or coated with a therapeutic agent or further includes at least one carrier, which may or may not be removable, which may include a medium, for example a metal or plastic mesh, or a surface, adapted to bear a therapeutic agent. The carrier may be a disc, tablet, or a liner that affixes to the inside of the tubular element. The these embodiments may include two opposite edges, and can include multi-edged configurations, for example as in a star shape. The tubular element further defines two or more opposing channels on an inner surface of the tubular element. The two or more opposing channels extend in a plane substantially parallel to the central axis and are adapted to receive the two or more opposite edges of said removable or permanently placed carrier. The therapeutic agent may be medications, for example, antibiotics, for treating chronic sinusitis or other nasal diseases.

In a further embodiment, the tubular element includes at least one substantially annular-shaped stiffening element affixed to the one or two ends of the tubular element, or to the middle portion of the tubular element. The tubular element may also include stiffening element with other configurations affixed to side wall of the tubular element. The varying shaped stiffening element is preferably embedded in the tubular element, but also can be attached to the inner or outer surface of the tubular element.

In a further preferred embodiment, the tubular element is made from a shape memory material.

BRIEF DESCRIPTION OF THE DRAWINGS

The foregoing and other objects of this invention, the various features thereof, as well as the invention itself, may be more fully understood from the following description, when read together with the accompanying drawings, in which:

FIGS. 13-21 depict additional devices embodying various disclosed features.

DETAILED DESCRIPTION

Figure 1:
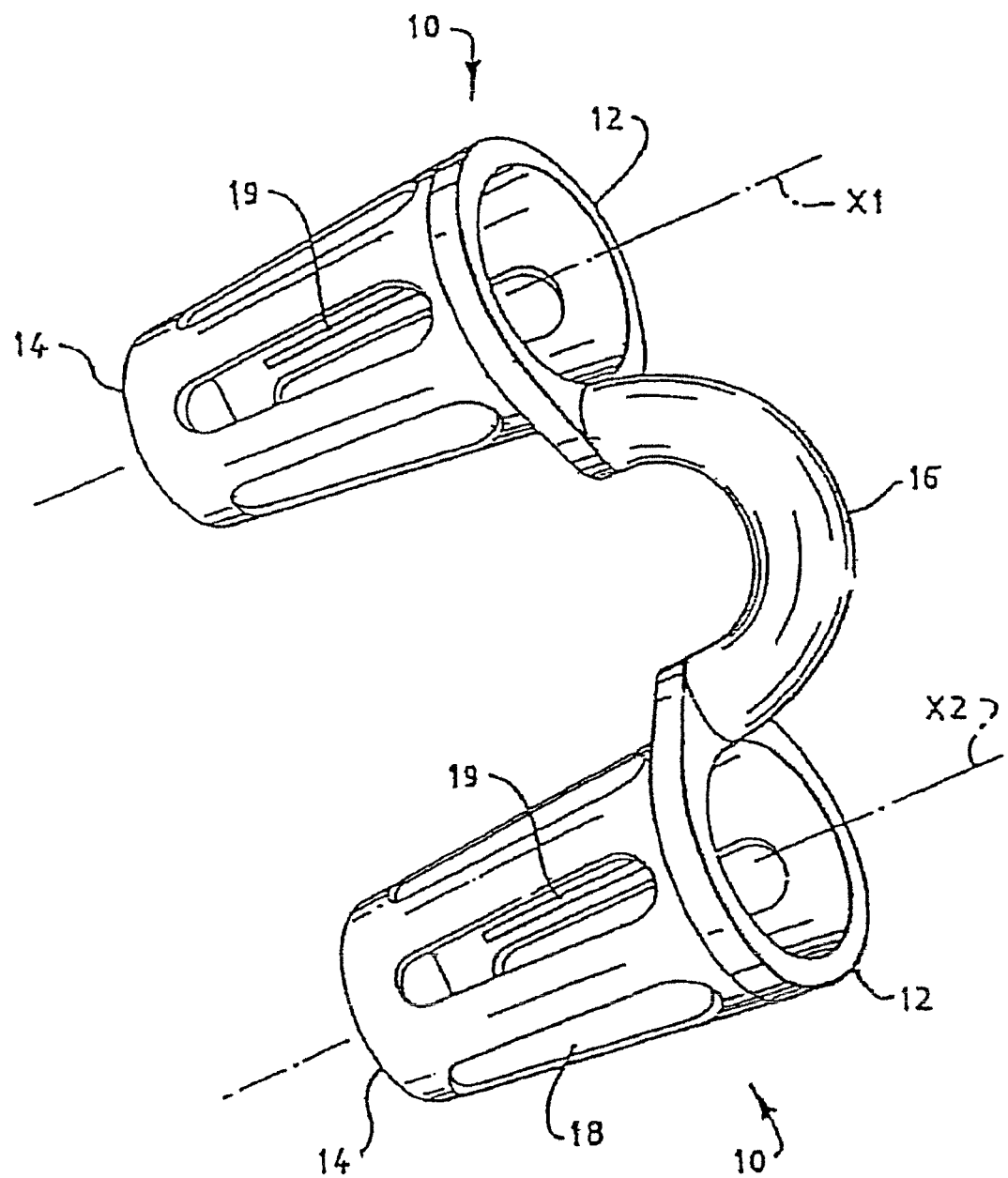
FIG. 1 is a perspective view of one embodiment of the present invention.

The nasal breathing assist devices according to the various aspects of the invention are shown in FIGS. 1 through 10. These devices overcome the deficiencies in the currently available devices. The illustrated devices are small, inconspicuous in use, and require no special attachments or fittings, although they may be combined with other devices, such as cannulas. The devices are worn inside the nose, so that the nasal passages are kept open from the inside, rather than by external means. This allows the devices to maintain airways in noses where nasal obstructions, inflammatory or structural anatomical deviations diminish the effectiveness of externally applied strips. The devices can be used alone, or in conjunction with decongestant and antihistamines powders, tablets or liquid medications, other snore-reducing aids, such as pillows, or medicated nasal sprays.

For convenience, before further description of exemplary embodiments, certain terms employed in the specification, examples, and appended claims are collected here. These definitions should be read in light of the remainder of the disclosure and understood as by a person of skill in the art.

The articles "a" and "an" are used herein to refer to one or to more than one (i.e., to at least one) of the grammatical object of the article. By way of example, "an element" means one element or more than one element.

The term "access device" is an art-recognized term and includes any medical device adapted for gaining or maintaining access to an anatomic area. Such devices are familiar to artisans in the medical and surgical fields. An access device may be a needle, a catheter, a cannula, a trocar, a tubing, a shunt, a drain, or an endoscope such as an otoscope, nasopharyngoscope, bronchoscope, or any other medical device suitable for entering or remaining positioned within the preselected anatomic area.

The terms "biocompatible polymer" and "biocompatibility" when used in relation to polymers are art-recognized. For example, biocompatible polymers include polymers that are generally neither themselves toxic to the host, nor degrade (if the polymer degrades) at a rate that produces monomeric or oligomeric subunits or other byproducts at toxic concentrations in the host. In certain embodiments, biodegradation generally involves degradation of the polymer in a host, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1M NaOH at 37° C. until complete degradation is observed. The solution is then neutralized with 1M HCl. About 200 μL of various concentrations of the degraded sample products are placed in 96-well tissue culture plates and seeded with human gastric carcinoma cells (GT3TKB) at $10^4$/well density. The degraded sample products are incubated with the GT3TKB cells for 48 hours. The results of the assay may be plotted as % relative growth vs. concentration of degraded sample in the tissue-culture well. In addition, polymers and formulations may also be evaluated by well-known in vivo tests, such as subcutaneous implantations in rats to confirm that they do not cause significant levels of irritation or inflammation at the subcutaneous implantation sites.

The term "biodegradable" is art-recognized, and includes polymers, compositions and formulations, such as those described herein, that are intended to degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to side chain or that connects a side chain to the polymer backbone. For example, a therapeutic agent or other chemical moiety attached as a side chain to the polymer backbone may be released by biodegradation. In certain embodiments, one or the other or both generally types of biodegradation may occur during use of a polymer. As used herein, the term "biodegradation" encompasses both general types of biodegradation.

The degradation rate of a biodegradable polymer often depends in part on a variety of factors, including the chemical identity of the linkage responsible for any degradation, the molecular weight, crystallinity, biostability, and degree of cross-linking of such polymer, the physical characteristics of the implant, shape and size, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible".

In certain embodiments, if the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of any such material incorporated therein.

In certain embodiments, polymeric formulations biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the polymer degrades in a period of between about one hour and several weeks, depending on the desired application.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "drug delivery device" is an art-recognized term and refers to any medical device suitable for the application of a drug to a targeted organ or anatomic region. The term includes those devices that transport or accomplish the instillation of the compositions towards the targeted organ or anatomic area, even if the device itself is not formulated to include the composition. As an example, a needle or a catheter through which the composition is inserted into an anatomic area or into a blood vessel or other structure related to the anatomic area is understood to be a drug delivery device. As a further example, a stent or a shunt or a catheter that has the composition included in its substance or coated on its surface is understood to be a drug delivery device.

When used with respect to a therapeutic agent or other material, the term "sustained release" is art-recognized. For example, a subject composition that releases a substance over time may exhibit sustained release characteristics, in contrast to a bolus type administration in which the entire amount of the substance is made biologically available at one time. For example, in particular embodiments, upon contact with body fluids including blood, tissue fluid, lymph or the like, the polymer matrices (formulated as provided herein and otherwise as known to one of skill in the art) may undergo gradual degradation (e.g., through hydrolysis) with concomitant release of any material incorporated therein, for a sustained or extended period (as compared to the release from a bolus). This release may result in prolonged delivery of therapeutically effective amounts of any incorporated a therapeutic agent. Sustained release will vary in certain embodiments as described in greater detail below.

The term "delivery agent" is an art-recognized term, and includes molecules that facilitate the intracellular delivery of a therapeutic agent or other material. Examples of delivery agents include: sterols (e.g., cholesterol) and lipids (e.g., a cationic lipid, virosome or liposome).

The term "or" as used herein should be understood to mean "and/or", unless the context clearly indicates otherwise.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intranasal, intraperitoneal, transtracheal, subcutaneous, subcuticular, intraarticular, subcapsular, subarachnoid, intraspinal and intrasternal injection and infusion.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "fluid" is art-recognized to refer to a non-solid state of matter in which the atoms or molecules are free to move in relation to each other, as in a gas or liquid. If unconstrained upon application, a fluid material may flow to assume the shape of the space available to it, covering for example, the surfaces of an excisional site or the dead space left under a flap. A fluid material may be inserted or injected into a limited portion of a space and then may flow to enter a larger portion of the space or its entirety. Such a material may be termed "flowable." This term is art-recognized and includes, for example, liquid compositions that are capable of being sprayed into a site; injected with a manually operated syringe fitted with, for example, a 23-gauge needle; or delivered through a catheter. Also included in the term "flowable" are those highly viscous, "gel-like" materials at room temperature that may be delivered to the desired site by pouring, squeezing from a tube, or being injected with any one of the commercially available injection devices that provide injection pressures sufficient to propel highly viscous materials through a delivery system such as a needle or a catheter. When the polymer used is itself flowable, a composition comprising it need not include a biocompatible solvent to allow its dispersion within a body cavity. Rather, the flowable polymer may be delivered into the body cavity using a delivery system that relies upon the native flowability of the material for its application to the desired tissue surfaces. For example, if flowable, a composition comprising polymers can be injected to form, after injection, a temporary biomechanical barrier to coat or encapsulate internal organs or tissues, or it can be used to produce coatings for solid implantable devices. In certain instances, flowable subject compositions have the ability to assume, over time, the shape of the space containing it at body temperature.

Viscosity is understood herein as it is recognized in the art to be the internal friction of a fluid or the resistance to flow exhibited by a fluid material when subjected to deformation. The degree of viscosity of the polymer may be adjusted by the molecular weight of the polymer and other methods for altering the physical characteristics of a specific polymer will be evident to practitioners of ordinary skill with no more than routine experimentation. The molecular weight of the polymer used may vary widely, depending on whether a rigid solid state (higher molecular weights) desirable, or whether a fluid state (lower molecular weights) is desired.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.*, 66:1-19 (1977).

A "patient," "subject," or "host" to be treated by the subject method may mean either a human or non-human animal, such as primates, mammals, and vertebrates.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a polymer, produces some desired effect at a reasonable benefit/risk ratio applicable to any medical treatment. In certain embodiments, the term refers to that amount necessary or sufficient to eliminate, reduce or maintain (e.g., prevent the spread of) a tumor or other target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation.

The term "preventing", when used in relation to a condition, such as a local recurrence, a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population.

"Radiosensitizer" is defined as a therapeutic agent that, upon administration in a therapeutically effective amount, promotes the treatment of one or more diseases or conditions that are treatable with electromagnetic radiation. In general, radiosensitizers are intended to be used in conjunction with electromagnetic radiation as part of a prophylactic or therapeutic treatment. Appropriate radiosensitizers to use in conjunction with treatment with the subject compositions will be known to those of skill in the art.

"Electromagnetic radiation" as used in this specification includes, but is not limited to, radiation having the wavelength of $10^{-20}$ to 10 meters. Particular embodiments of electromagnetic radiation employ the electromagnetic radiation of: gamma-radiation ($10^{-20}$ to $10^{-13}$ m), x-ray radiation ($10^{-11}$ to $10^{-9}$ m), ultraviolet light (10 nm to 400 nm), visible light (400 nm to 700 nm), infrared radiation (700 nm to 1.0 mm), and microwave radiation (1 mm to 30 cm).

The phrases "systemic administration," "administered systemically," "peripheral administration" and "administered peripherally" are art-recognized, and include the administration of a subject composition or other material at a site remote from the disease being treated. Administration of an agent directly into, onto or in the vicinity of a lesion of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

In certain embodiments, a therapeutically effective amount of a therapeutic agent for in vivo use will likely depend on a number of factors, including: the rate of release of the agent from the polymer matrix, which will depend in part on the chemical and physical characteristics of the polymer; the identity of the agent; the mode and method of administration; and any other materials incorporated in the polymer matrix in addition to the agent.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The terms "incorporated" and "encapsulated" are art-recognized when used in reference to a therapeutic agent and a polymeric composition, such as a composition disclosed herein. In certain embodiments, these terms include incorporating, formulating or otherwise including such agent into a composition which allows for sustained release of such agent in the desired application. The terms may contemplate any manner by which a therapeutic agent or other material is incorporated into a polymer matrix, including for example: attached to a monomer of such polymer (by covalent or other binding interaction) and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other a therapeutic agent or other material in a subject composition.

More specifically, the physical form in which a therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in a controlled-release polymer that it is dispersed as small droplets, rather than being dissolved, in the polymer. Any form of encapsulation or incorporation is contemplated by the present disclosure, in so much as the sustained release of any encapsulated therapeutic agent or other material determines whether the form of encapsulation is sufficiently acceptable for any particular use.

The term "biocompatible plasticizer" is art-recognized, and includes materials which are soluble or dispersible in the controlled-release compositions described herein, which increase the flexibility of the polymer matrix, and which, in the amounts employed, are biocompatible. Suitable plasticizers are well known in the art and include those disclosed in U.S. Pat. Nos. 2,784,127 and 4,444,933. Specific plasticizers include, by way of example, acetyl tri-n-butyl citrate (c. 20 weight percent or less), acetyl trihexyl citrate (c. 20 weight percent or less), butyl benzyl phthalate, dibutyl phthalate, dioctylphthalate, n-butyryl tri-n-hexyl citrate, diethylene glycol dibenzoate (c. 20 weight percent or less) and the like.

"Small molecule" is an art-recognized term. In certain embodiments, this term refers to a molecule which has a molecular weight of less than about 2000 amu, or less than about 1000 amu, and even less than about 500 amu.

In the embodiment shown in FIG. 1, the nasal breathing assist device 1 comprises generally a pair of open ended tubular elements 10 connected together by a coupler element 16.

The tubular elements 10 are generally circular in cross section and extend a distance along tube axes X1 and X2 from first ends 12 to second ends 14. Preferably the tubular elements taper linearly from a relatively large diameter cross section along the tube axes X1 and X2 to a relatively smaller diameter cross section from the first end 12 to the second end 14. The taper may be other than linear, for example, contoured to correspond generally to the taper inside the user's nostrils. First ends 12 also connect to the coupler element 16. In the illustrated form, the tubular elements 10 are conicfrustums, but other shapes may be used. For example, instead of circular cross sections, the tubular elements could have elliptical or other shaped cross sections. Further, instead of the inner diameter tapering monotonically from the large end to the small end, it could decrease initially, become larger, then decrease again.

The tubular elements 10 may also include at least one passageway 18 extending through the walls of the tubular elements transverse to the tube axes X1 and X2. The passageways 18 may be circular, elliptical, or elongated at least in part in the direction of the tube axes. Alternately, the passageways can be elongated in a direction extending circumferentially around the tube axes.

The coupler element 16 is a resilient, nominally curved strut which maintains the tubular elements spaced apart, with axes X1 and X2 in a substantially parallel relationship, and in substantially a common plane. The coupler element may be made of resilient, semi-rigid, or rigid material.

Grooves 19 inside of tubular elements are an additional feature which may be used to receive medication (nasal cream) before inserting in nasal passage so as not to irritate the skin inside the nasal passage, this allows the medication to be effective without contacting the nasal passage.

Figure 2:
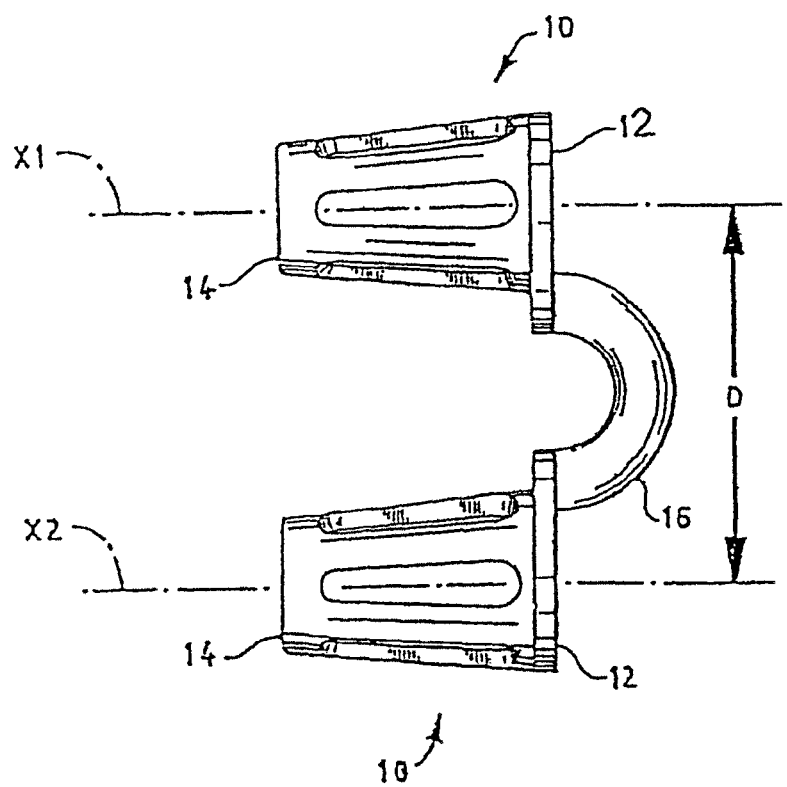
FIG. 2 shows a side view of the embodiment shown in FIG. 1.
Figure 3A:
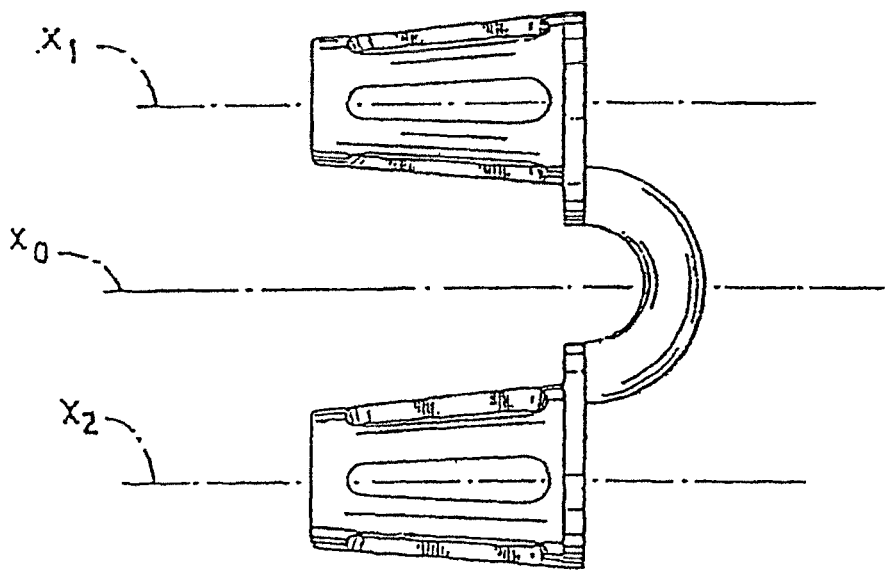
FIG. 3A shows a side view of an alternate embodiment of the invention.
Figure 3B:
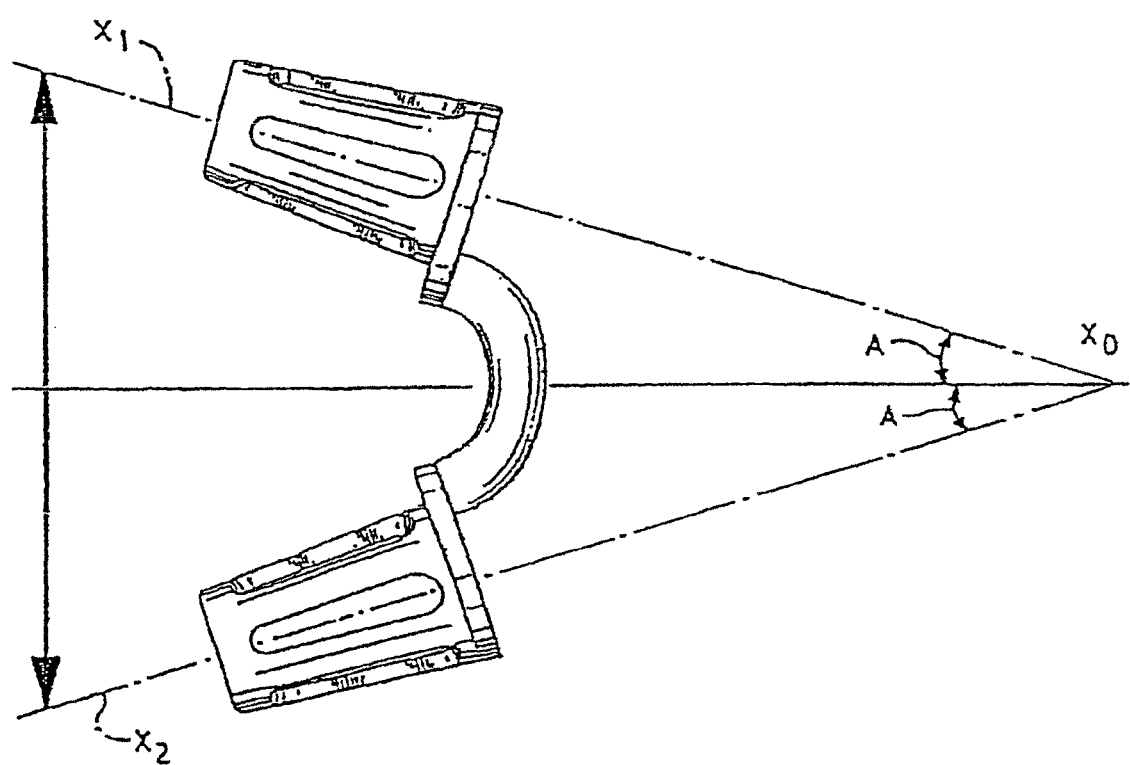
FIG. 3B shows a side view of the embodiment of FIG. 3A rotated about an axis.

As shown in FIG. 2, coupler element 16 maintains a nominal distance D between the tubular elements 10 that generally corresponds to the distance between the user's nostrils. In this embodiment, the coupler element extends in a plane that is essentially parallel to tube axes X1 and X2. As shown in FIGS. 3A and 3B, the resistance of coupler element 16 permits the axes X1 and X2 to be offset from an axis $X_0$ by angle A. Angle A can be as much as 15° or greater. Furthermore, in this embodiment, coupler element 16 permits relative flexing motion of the device about an axis, substantially perpendicular to the tube axes X1 and X2.

Figure 4A:
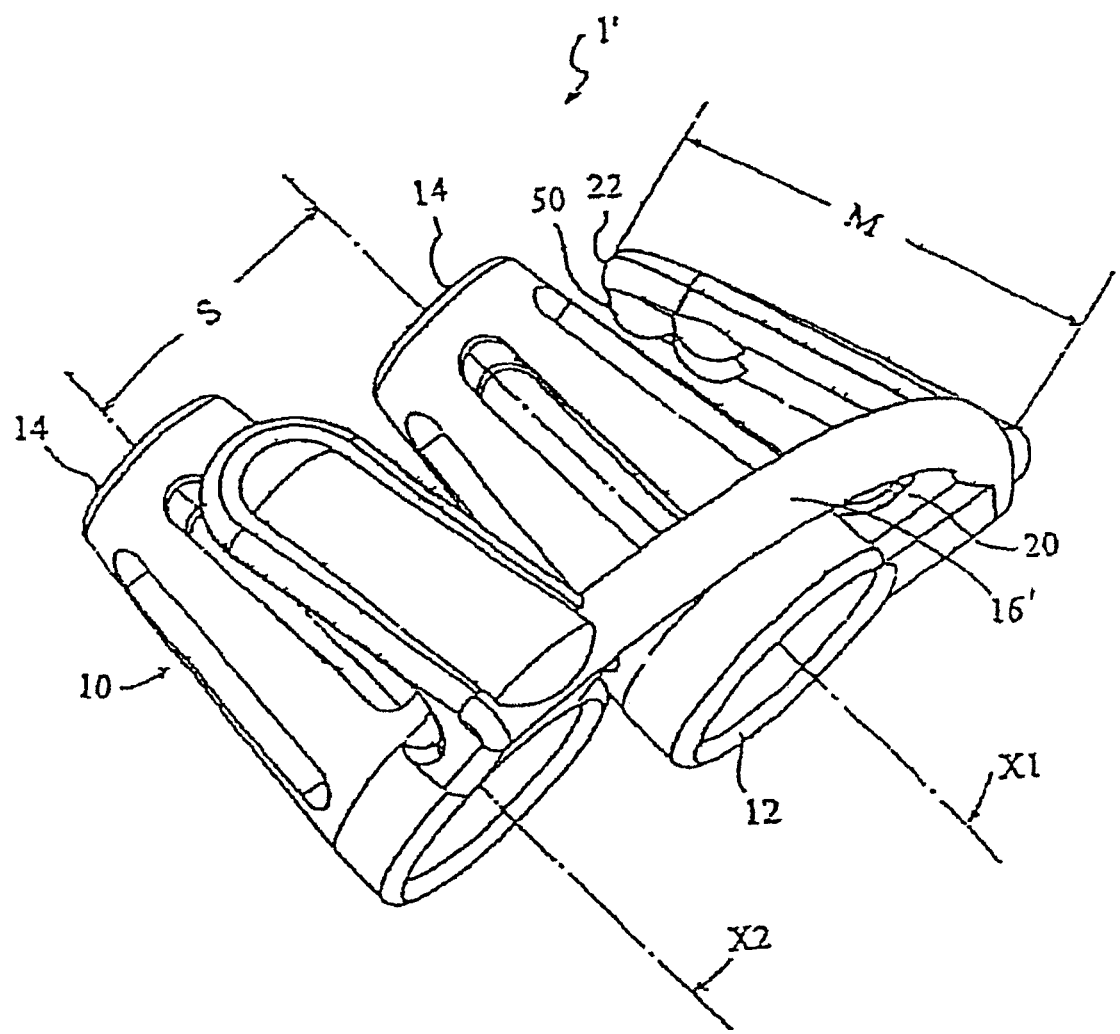
FIG. 4A is a perspective view of an alternate embodiment of the invention.

In a preferred embodiment shown in FIG. 4A, device 1' has coupler element 16' which extends between first ends 12. The central axis of coupler element 16' lies in a plane that is substantially perpendicular to the tube axes X1 and X2. In this embodiment, coupler element 16' permits relative flexing motion of device 1' so that axes X1 and X2 remain substantially parallel, but separation S of those axes varies to accommodate spacing of the nostrils.

Radially extending tab supports 20 extend from first ends 12 and connect to coupler element 16. Tabs 22 extend from tab supports 20 a distance M in the direction of the central axis to distal ends of the tabs. Tabs 22 are preferably made of non-resiliently deformable materials, for example, metal including copper, aluminum, and etc. The tab supports 20 may be made of the same or different materials as that used for the tabs 22. In use, tabs 22 remain outside the user's nostrils, and, acting as clips, help secure the device in the nostrils. The tabs 22 also function as a stop which prevent the device from being wholly inserted into a user's nostril.

Figure 4B:
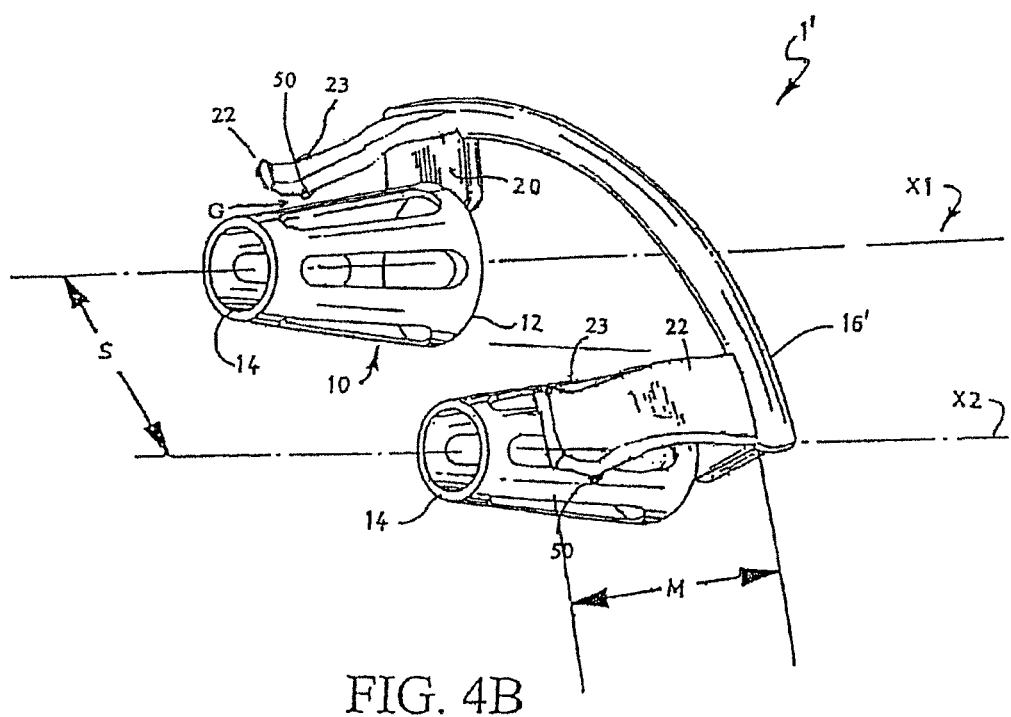
FIG. 4B is a perspective view of another alternate embodiment of the invention.

In another preferred embodiment, as shown in FIG. 4B, the tabs 22 are substantially S-shaped, and includes a distal curved portion 23 distal from the first end 12. The distal curved portion 23 defines a relatively small gap G with an outer surface of the tubular element. The tabs 22 are constructed such that the small gap G is adapted to receive a lateral wall of a user's nose, and the tabs 22 are adapted to clip on the lateral wall of the user's nose. In one preferred embodiment, the tab 22 includes at least one relatively small protrusion 50 extending from the distal curved portion 23 toward the tubular element 10, as best shown in FIG. 4B and FIG. 5B. Alternatively, the relatively small protrusion 50 may extend from the outer surface of the tubular element 10 toward the distal curved portion 23 of the tab 22. In another alternate embodiment, the tab 22 includes protrusions 50 extending from the distal curved portion 23 toward the tubular element 10, and the tubular element 10 also includes protrusions opposing to the protrusions of the tab 22. In the embodiment shown in FIG. 4A, the protrusions 50 extends from a distal end of the tab 22 toward the tubular element 10. The small protrusion helps to secure the device in the user's nostrils.

Figure 5A:
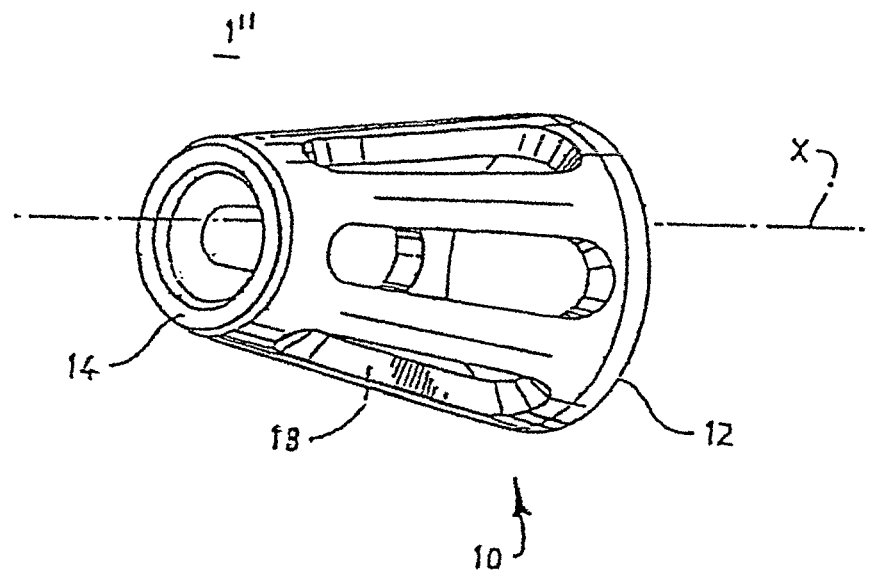
FIG. 5A is a perspective view of an alternate embodiment of the invention.
Figure 5B:
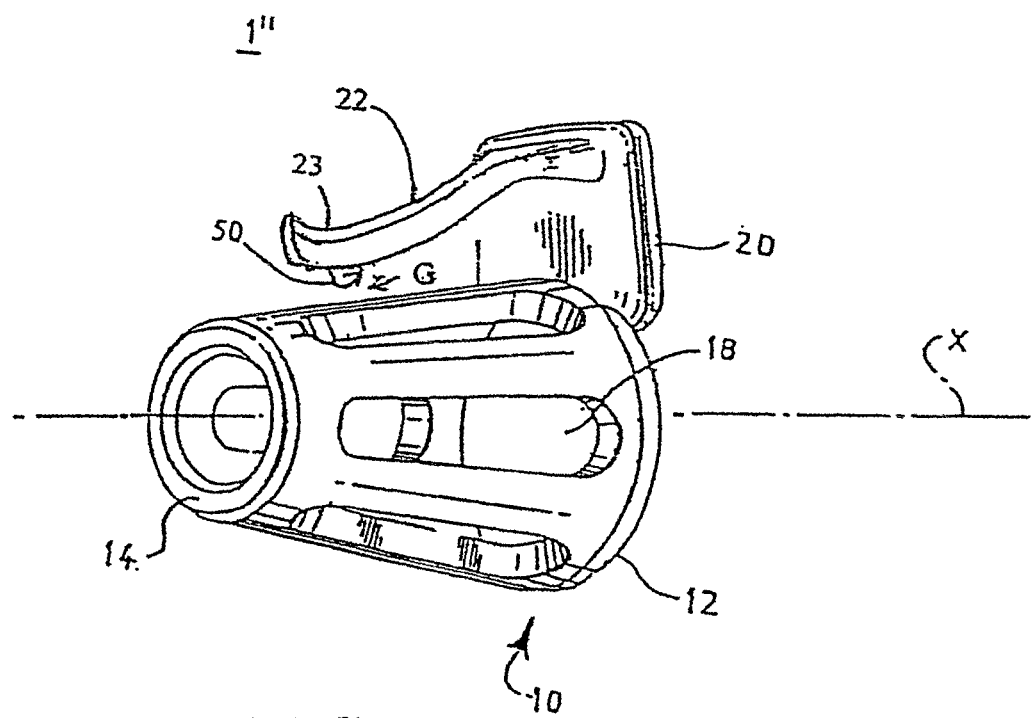
FIG. 5B is a perspective view of yet another embodiment of the invention.

FIGS. 5A-5E show other embodiments of nasal breathing assist devices. In FIG. 5A, device 1" has a tubular element 10 extending along a tube axis X between a relatively large diameter first end 12 and tapering toward a relatively smaller diameter second end 14. As previously described, tubular element 10 may have passageways 18 extending through the walls of the tubular elements transverse to tube axis X.

Figure 5C:
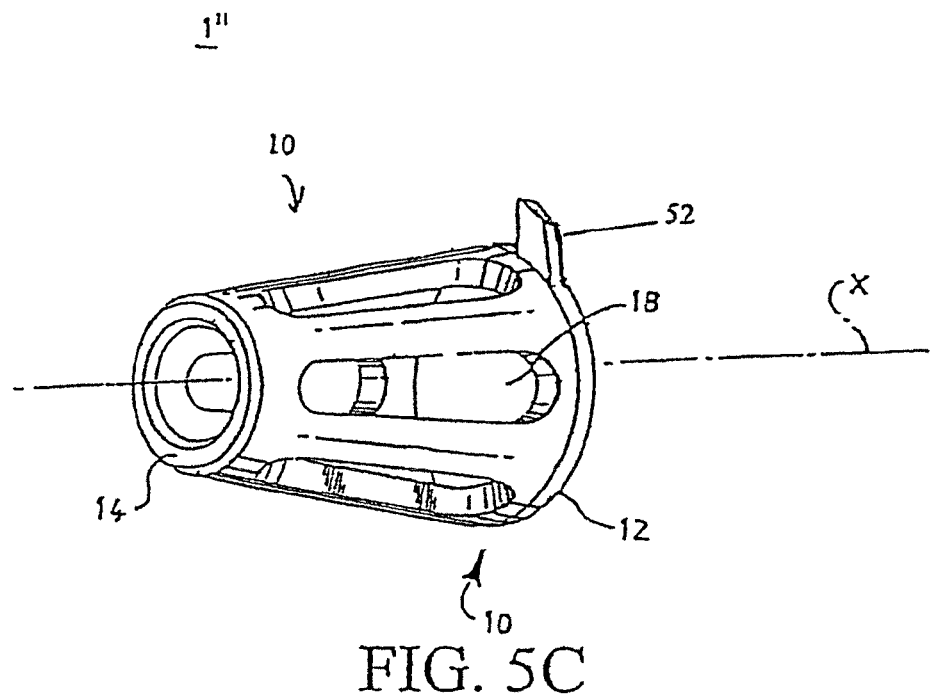
FIG. 5C is a perspective view of another embodiment of the invention.
Figure 5D:
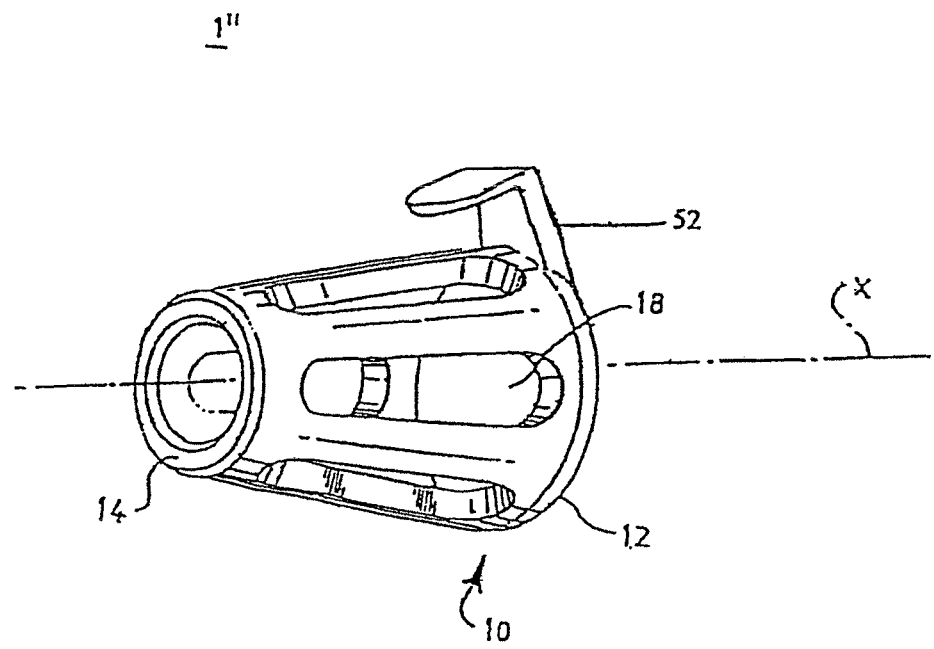
FIG. 5D is a perspective view of another embodiment of the invention.
Figure 5E:
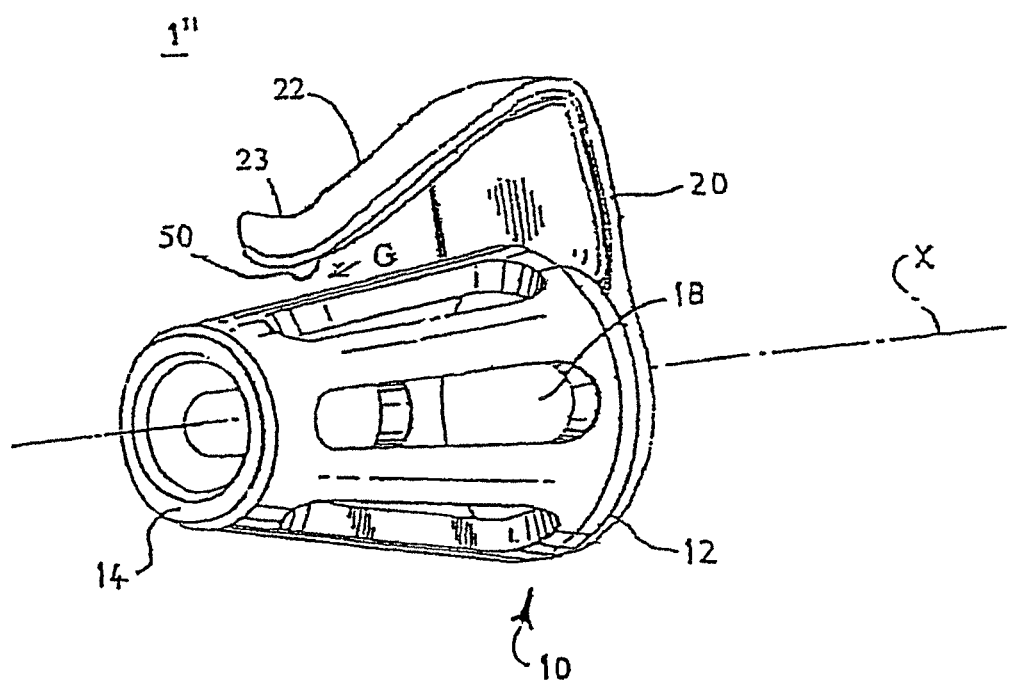
FIG. 5E is a perspective view of another embodiment of the invention.

As shown in the embodiment in FIG. 5B, radially extending tab support 20 extends from first end 12. The substantially S-shaped non-resilient tab 22 extends from tab support 20 a distance M in the direction of axis X toward second end 14. FIG. 5C illustrates another preferred embodiment, in which the device includes a stop member 52 extending radially and outwardly from the first end 12 of the tubular element to a distal end. The stop member 52 is adapted to engage with an open end of a user's nostril to prevent the device from being wholly inserted into the nostril when the device is in use. In an alternate embodiment, as shown in FIG. 5D, the stop member may further include a protrusion extending from the distal end of the stop member toward the second 14 of the tubular element 10. In another alternate embodiment, as shown in FIG. 5E, the substantially S-shaped non-resilient tab 22, the tab support 20, and the tubular element 10 are integrally constructed. In use, the protrusion remains outside the user's nostril, and, acting as a clip, helps secure the device in the nostril. Device 1" of FIGS. 5A-5E may be used singly or as a pair. The stop member 52 may also be employed in the embodiments having a pair of tubular elements connected by a coupler element.

Figure 10A:
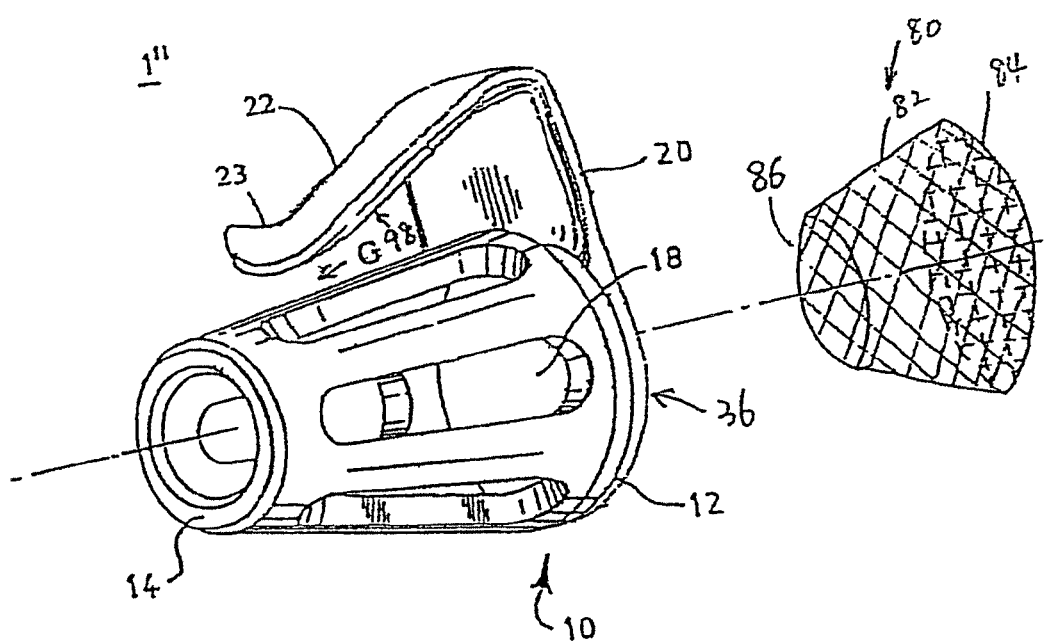
FIG. 10A shows a schematic view of a filter in accordance with one preferred embodiment of the present invention.
Figure 10B:
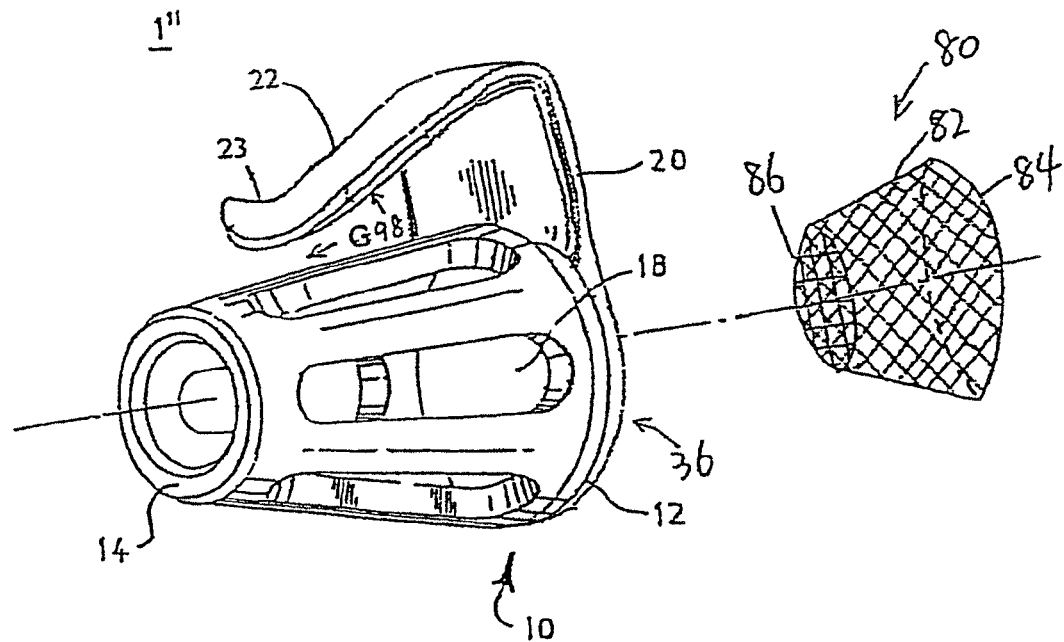
FIG. 10B shows a schematic view of a filter in accordance with another preferred embodiment of the present invention.

In another preferred embodiment, the tab 22 has an inner surface, which faces the tubular element and is at least partially coated with adhesive 98, as shown in FIGS. 10A and 10B. The tab 22 is also preferably non-resiliently deformable. In use, after the device is inserted into a user's nostrils and the tab 22 is pressed against the outer surface the user's nose, the tab 22 keeps in contact with the outer surface of the user's nose. The adhesive coating increases the friction between the tab 22 and the outer surface of the user's nose, and make the tab to stick to the outer surface of the user's nose, thus increasing the stability of the device within the user's nose. The adhesive coating of the inner surface of the tab helps to maintain the device within a user's nose, preventing the device from being knocked off during sleep, sports, or other activities.

Figure 6:
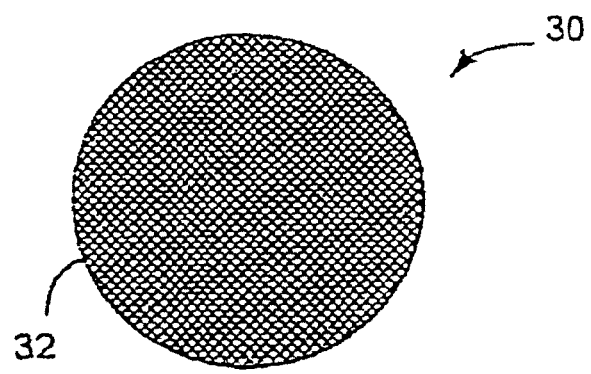
FIG. 6 shows a schematic view of a filter in accordance with one embodiment of the present invention.

FIG. 6 shows a filter 30 which may be used with the nasal breathing assist device. The filter 30 includes a filter medium, preferably a paper, a metal or plastic mesh coated with absorbent materials, spanning a frame 32. The frame 32 is preferably contoured to fit in an open-faced inner channel 36 defined in the tubular element 10. In a preferred embodiment, the tubular element 10 includes at least one relatively small protrusion 38 extending radially from an inner surface of the inner channel 36. The frame 32 of the filter 30 is adapted to snap-fit over the protrusion 38 into the inner channel 36 and is retained by the protrusion 38, thereby the filter 30 cannot slip out of the tubular element 10 when the nasal breathing assist device is in use. A filter may be secured to a device in several other ways, such as by adhesive, snap-fitting, press-fitting, integral molding, twist-locking, sliding into groove(s) 19, and/or by use of hook-and-loop fasteners (such as VELCRO® brand fasteners).

Figure 7:
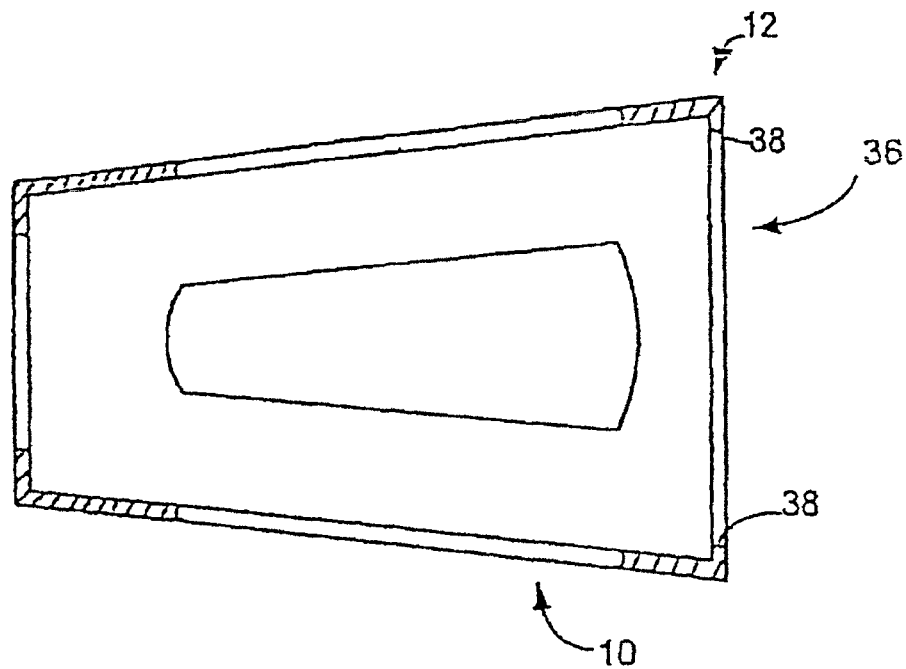
FIG. 7 shows a cross-sectional view of an alternate embodiment of the invention.
Figure 8:
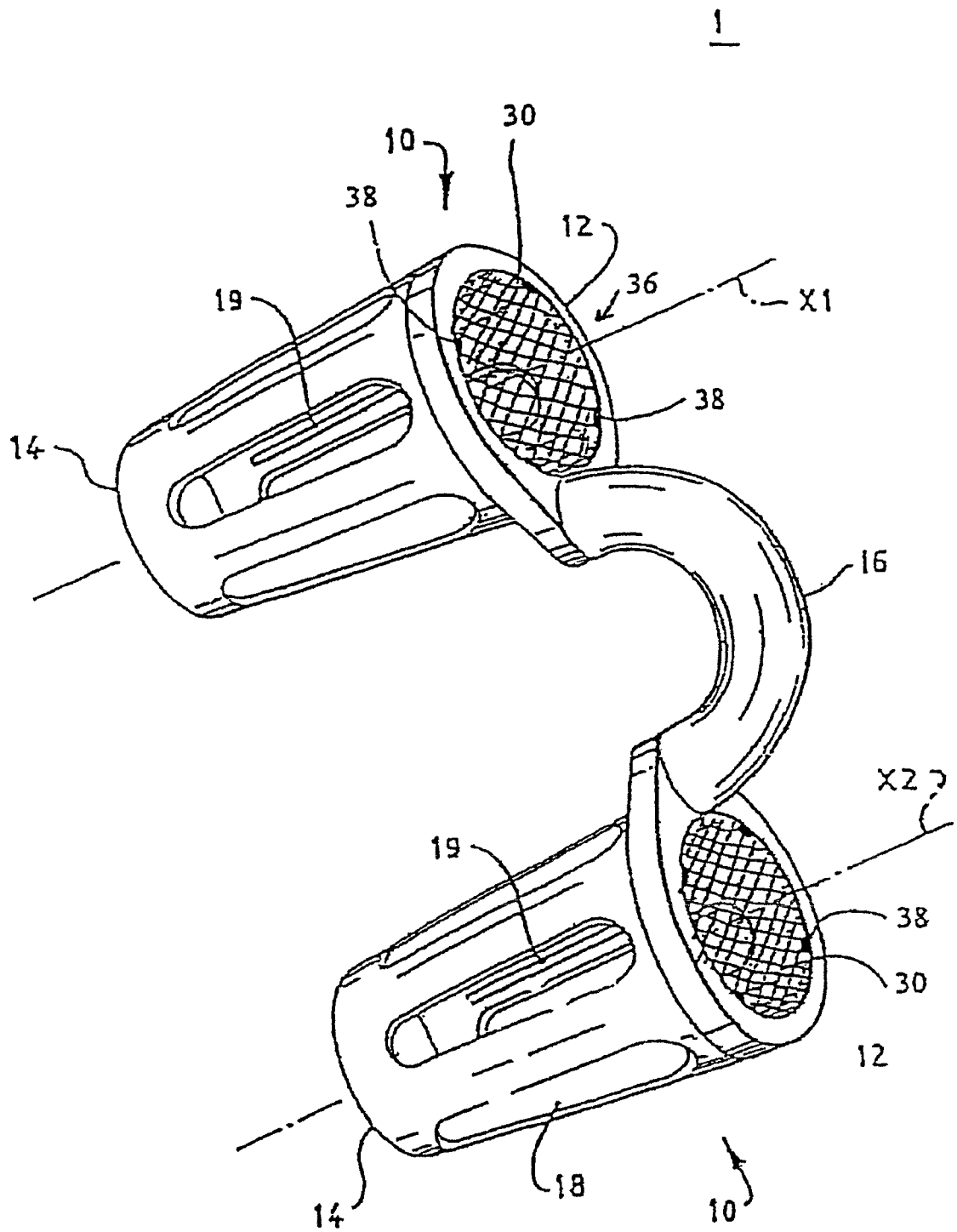
FIG. 8 shows the filter of FIG. 6 together with the nasal breathing assist device.

FIG. 7 illustrates a cross-sectional view of one tubular element 10 in accordance with one preferred embodiment of the invention. As shown in FIG. 7, the protrusion 38 extends throughout an inner circumference at the first end 12 (the end with a relatively large diameter) of the inner channel 36. The filter 30 is snap-plugged into the channel 36 from the first end of the channel 36, and because the diameter of the channel 36 tapers from the first end to the second end, the filter can be secured by the inner surface of the channel 36 and the protrusion 38. The protrusion 38 is relatively small, so that the filter 36 can by easily removed and replaced. FIG. 8 shows a schematic view of the filters 30 together with a nasal breathing assist device. Each tubular element 10 includes relatively small protrusions 38 securing the filter 30 at the first end of the tubular element 10. The filter 30 is preferably positioned at one of the two ends of the tubular element 10, so that the filter 30 can be easily removed and replaced, but the filter 30 also can be positioned at a place between the two ends and secured by protrusions extending radially adjacent that place.

Figure 9:
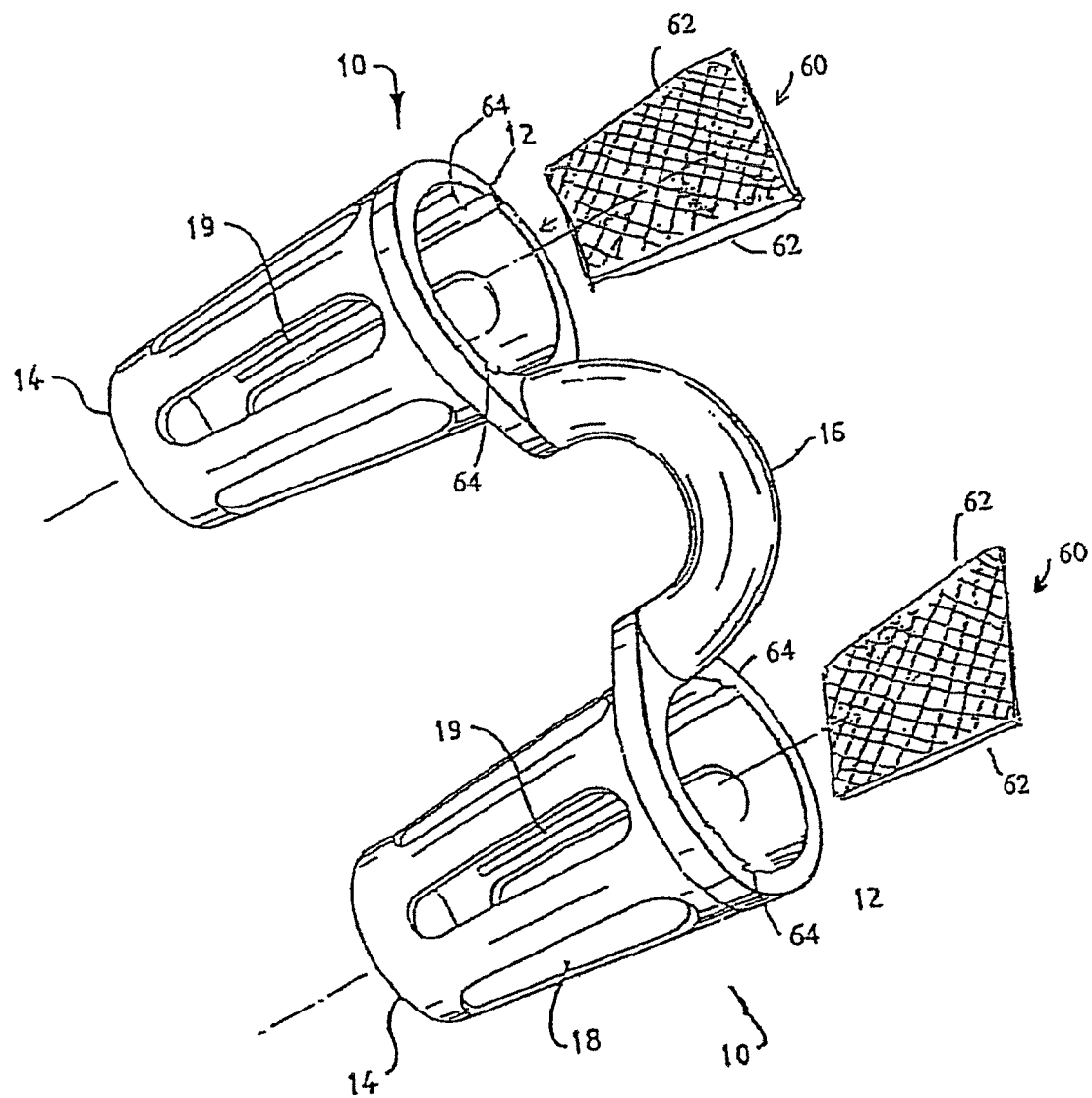
FIG. 9 shows another preferred embodiment of the invention.

FIG. 9 illustrates another preferred embodiment of the present invention. As shown in FIG. 9, The device further includes at least one removable medication carrier 60 which may include a medium adapted to bear a therapeutic agent. The removable carrier 60 preferably includes a frame tapering from a first end to a second end. The frame includes two opposite edges 62. The tubular element 10 further defines two opposing channels 64 on an inner surface of the tubular element 10. The two opposing channels 64 extend substantially in the same direction as the central axis and are adapted to receive the two opposite edges 62 of said removable carrier 60. The frame of the removable medication carrier 60 may be constructed with other shapes, and the tubular element may define corresponding channels or other mechanism for receiving the frame of the carrier 60. The therapeutic agent may be medications, for example, antibiotics, for treating chronic sinusitis or other nasal diseases.

In alternative embodiments, as illustrated in FIGS. 10A and 10B, the filter is a liner filter (as denoted by number 80 in FIGS. 10A and 10B) including a conic-shaped liner portion 82 extending between two ends 84 and 86. One end has a relatively large diameter and the other end has a relatively small diameter. In the embodiment shown in FIG. 10A, the relatively large end 84 is a closed end having a filter medium spanning the circumference of the end of the liner portion, and the other end 86 is an opened end. In an alternative form, as shown in FIG. 10B, the filter medium is attached to the relatively small end 86, and the relative large end is an open-faced end.

The liner portion 82, preferably but not necessarily, is constructed by the filter medium. The filter 80 preferably but not necessarily is made from a unitary sheet of a filter medium by a molding process. The filter 80 is sized to fit in the open-faced inner channel 36 defined in the tubular element 10. The tubular element 10 may include at least one relatively small protrusion extending radially from an inner surface of the inner channel 36 at the relatively large end of the tubular element for preventing the liner filter 80 from slipping out of the channel 36 of the tubular element 10. In use, the liner filter 80 is inserted into and retained in the inner channel 36 of the tubular element 10. The liner filter 80 can be easily removed from the inner channel 36, and can be replaced or cleaned.

The filter medium is constructed to filter pollen, dust, mold, and/or other particles that may cause allergic reactions or other diseases or discomfort. In an alternative form, the filter medium is preferably made from a material that can be coated with medications, particularly, medications for treating nasal diseases. Exemplary medications include decongestants, antihistamine, and antibiotic.

The filters as illustrated in FIGS. 6-8, the medication carriers shown in FIG. 9, and the liner filters as shown in FIGS. 10A and 10B can be used with nasal breathing assist devices, which have one tubular element or have a pair of tubular elements connected by a strut, as described in the previous embodiments. The nasal breathing assist devices can be disposable or reusable. The reusable devices can be easily cleaned by rinsing, washing, or scrubbing with water, such as hot tap water, with soap and water, with isopropyl alcohol, or by steam sterilizing (such as by microwave sterilizer), autoclaving, or boiling in tap water.

Figure 11A:
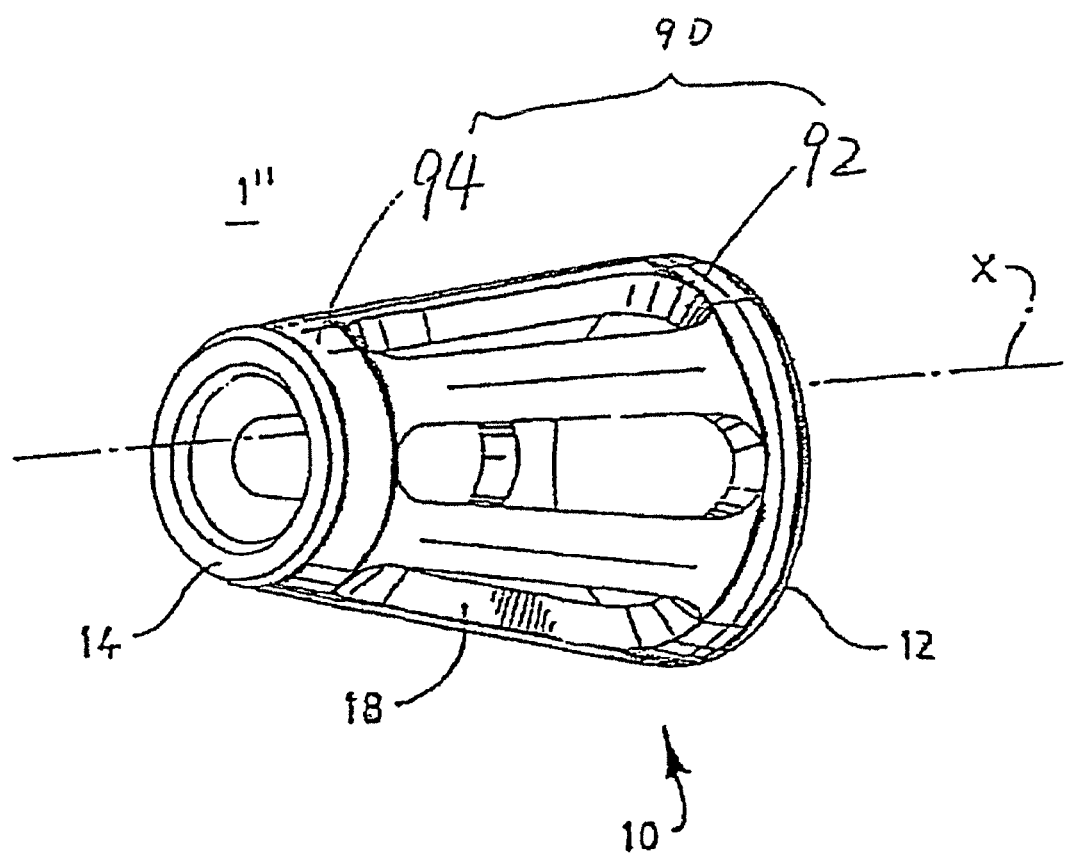
FIG. 11A shows a perspective view of another preferred embodiment of the present invention.

The device can be made of rigid, semi-resilient, or resilient materials. In one preferred embodiment, the tubular element 10 includes at least one stiffening element 90 embedded in or attached to the tubular element. The stiffening element 90 is preferably made from a material with a higher hardness value than the rest part of the tubular element 10. In one preferred form, as shown in FIG. 11A, the stiffening element 90 includes two rigid rings 92, 94 extending about the central axis of the tubular element 10 and embedded in the conic wall of the tubular element 10, one of the two rings, for example, the ring 92, preferably embedded at or near the relatively large end of the tubular element 10, and the other (ring 94) embedded at or near the relatively small end of the tubular element 10. The device could include more than two stiffening rings, and/or other shape stiffening parts embedded in the conic wall of the tubular element 10. Alternatively, the stiffening element 90 also can be attached to the inner surface or outer surface of the tubular element 10. The stiffening element prevents the tubular element 10 from collapse when under pressure and maintain opening of the nasal passage in severe cases, for example, pathologic nasal valve collapse, septal deviation, and other types of nasal congestion or obstruction. The stiffening element also increases the resilience of the tubular element 10 and the stability of the tubular element 10 within a user's nostrils.

Figure 11B:
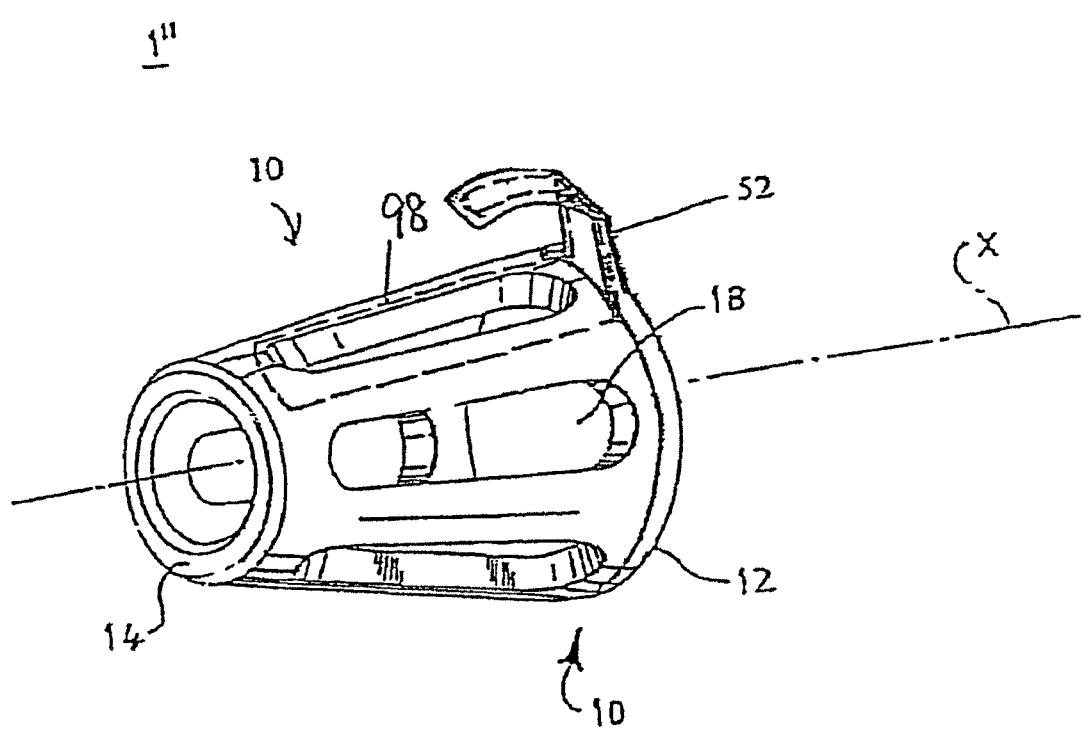
FIG. 11B shows a perspective view of another preferred embodiment of the present invention.

In another preferred embodiment, as shown in FIG. 11B, the stiffening element 90 includes an elongated wire embedded within the tubular element 10 and the tab 22.

In one preferred embodiment, part of the device is made from a non-resiliently deformable material, for example, aluminum. Preferably, the tabs 22 shown in FIGS. 4A-5E are made from a non-resiliently deformable material. In another preferred embodiment, as shown in FIG. 11B, an elongated metal wire is embedded within the tubular element 10 and the tab 22. In one preferred form, the wire is non-resiliently deformable, enabling the tab 22 non-resiliently deformable. In another preferred form, the wire is made from a resilient material, enabling the tab 22 resiliently deformable. In use, after the device is inserted to a user's nostrils, the user can force the tab 22 toward the outer surface of the user's nose to allow the tab 22 to touch the outer surface of the user's nose. The tab 22 will stay in contact with the outer surface of the user's nose, thus preventing the device from slipping out of the user's nose.

In a further preferred embodiment, at least part of the device is made from a shape memory material, such as a nickel-titanium alloy. For example, the device may have one shape under room temperature, and after the device is inserted into the user's nostrils, where the temperature is normally higher than the room temperature, the device returns to its original shape that fit the contour of the inside of the user's nostrils. The device may also be coated, or embedded with medications for treating nasal diseases, or other diseases, such as skin or mucous diseases.

Figure 12:
FIG. 12 is a representation of one embodiment of the invention in use.

The nasal breathing assist device is inserted in the user's nostrils, as shown in FIG. 12, usually at bedtime. The tubular elements maintain open nasal passages during sleeping, which allow the patient to obtain sufficient airflow through the nose only, rather than supplementing the air supply through the mouth. The filters can be made to absorb or hold pollen, dust, particles in smoke and smog fumes, nicotine in tobacco smoke, obnoxious odors, and other irritating elements.

FIGS. 13-21 depict nasal devices embodying additional features. These additional features may or may not be combined, as desired, with features described elsewhere in this disclosure.

Figure 13:
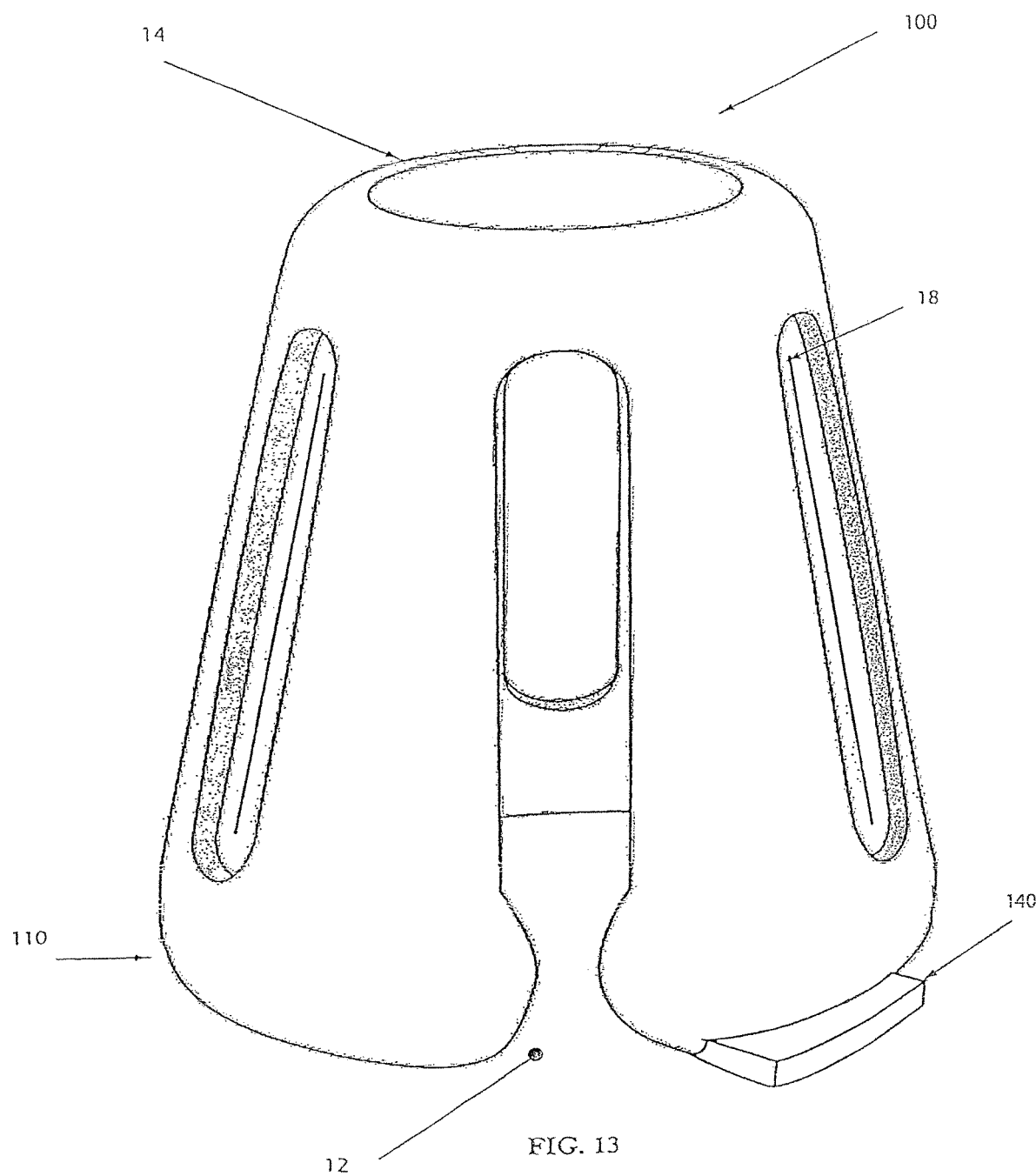
Figure 14:
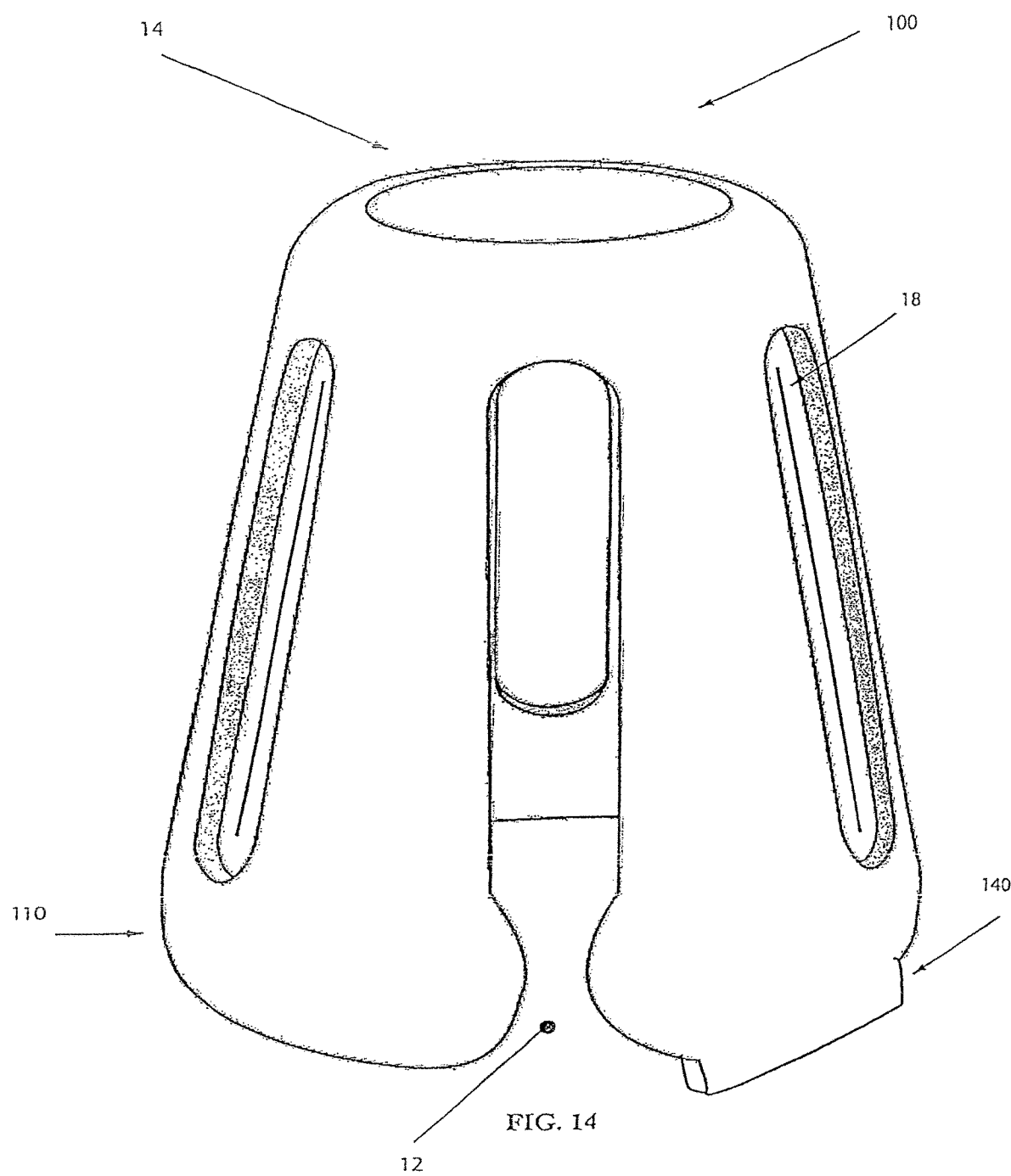

FIG. 13 depicts a device 100 having a roughly frusto-conical, dome-like, or cylindrical shape. The device includes a wall having a first end 12 and a second end 14. The wall may define one or more passageways 18 as described previously. The first and second ends define openings that allow passage of air or the positioning of insert(s), as described previously. The diameter, diagonal measure, and/or cross-sectional area of the second end may be smaller than that of the first end, to facilitate positioning of the device in, for example, a nostril. The first end portion of the wall defines a break 130, so that the first end opening is not completely encircled. The break may be continuous with a passageway, as shown. The break may increase the flexibility of the device. The second end need not define a break and may instead completely encircle the second end opening. The device may also include a foot 140 protruding from the first end. The foot may protrude outward as shown in FIG. 13, downward as shown in FIG. 14, or at intermediate angles. The foot may be rigidly positioned or may be flexible so that it can be positioned selectively. The foot may be so formed as to permit its remaining at a selected orientation, such as by embedding a metal wire or ribbon in the foot. The foot itself may be malleable to permit adjustment.

Figure 15:
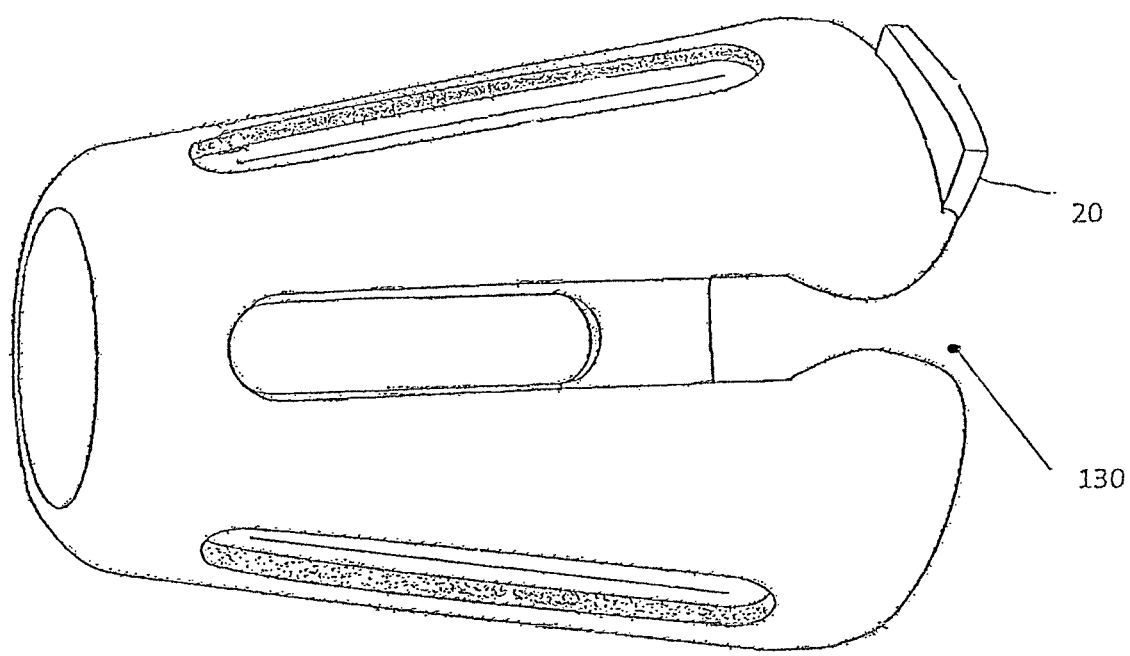

FIG. 15 depicts another embodiment of a device in which the second end defines a break 130, and the device includes a tab support 20. The device may further include a tab (not shown), which may be used to clip the device to a subject's nose, for example.

Figure 16:
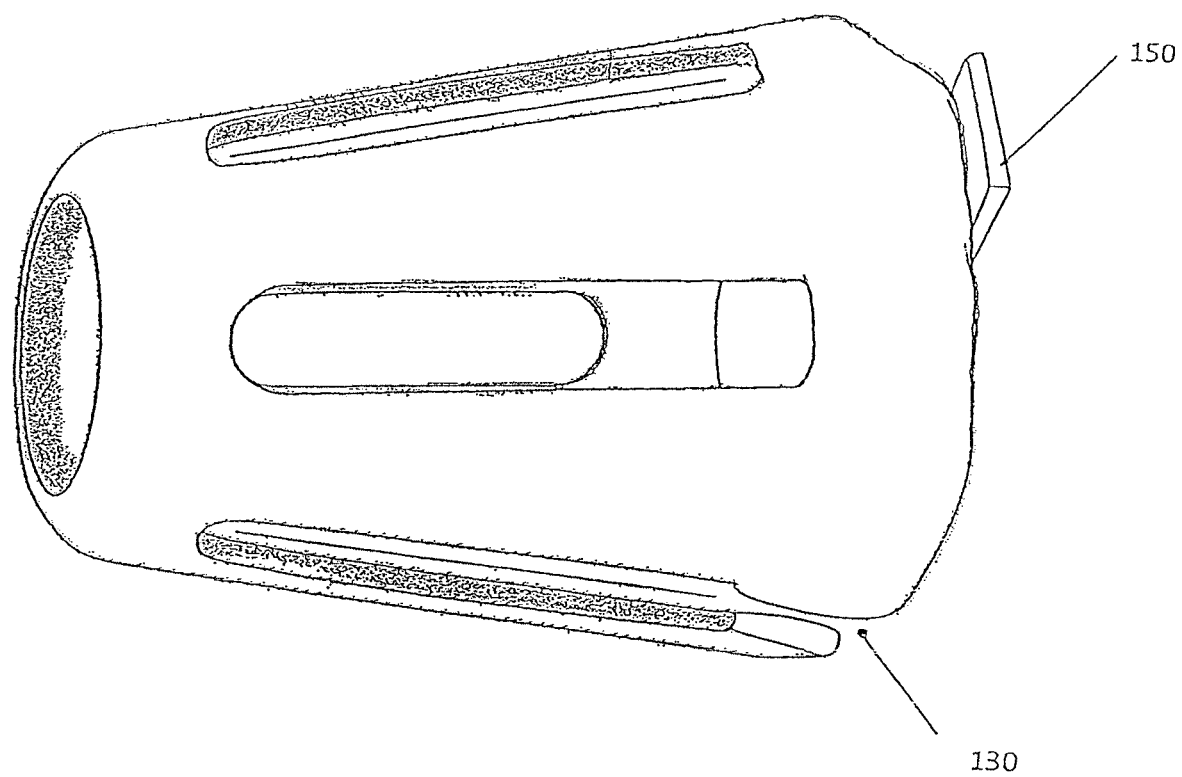

FIG. 16 depicts yet another embodiment of a device in which the break 130 is positioned at some distance away from feature 150 (such as foot 140 or tab support 20). The break may, but need not, be adjacent feature 150.

Figure 17:
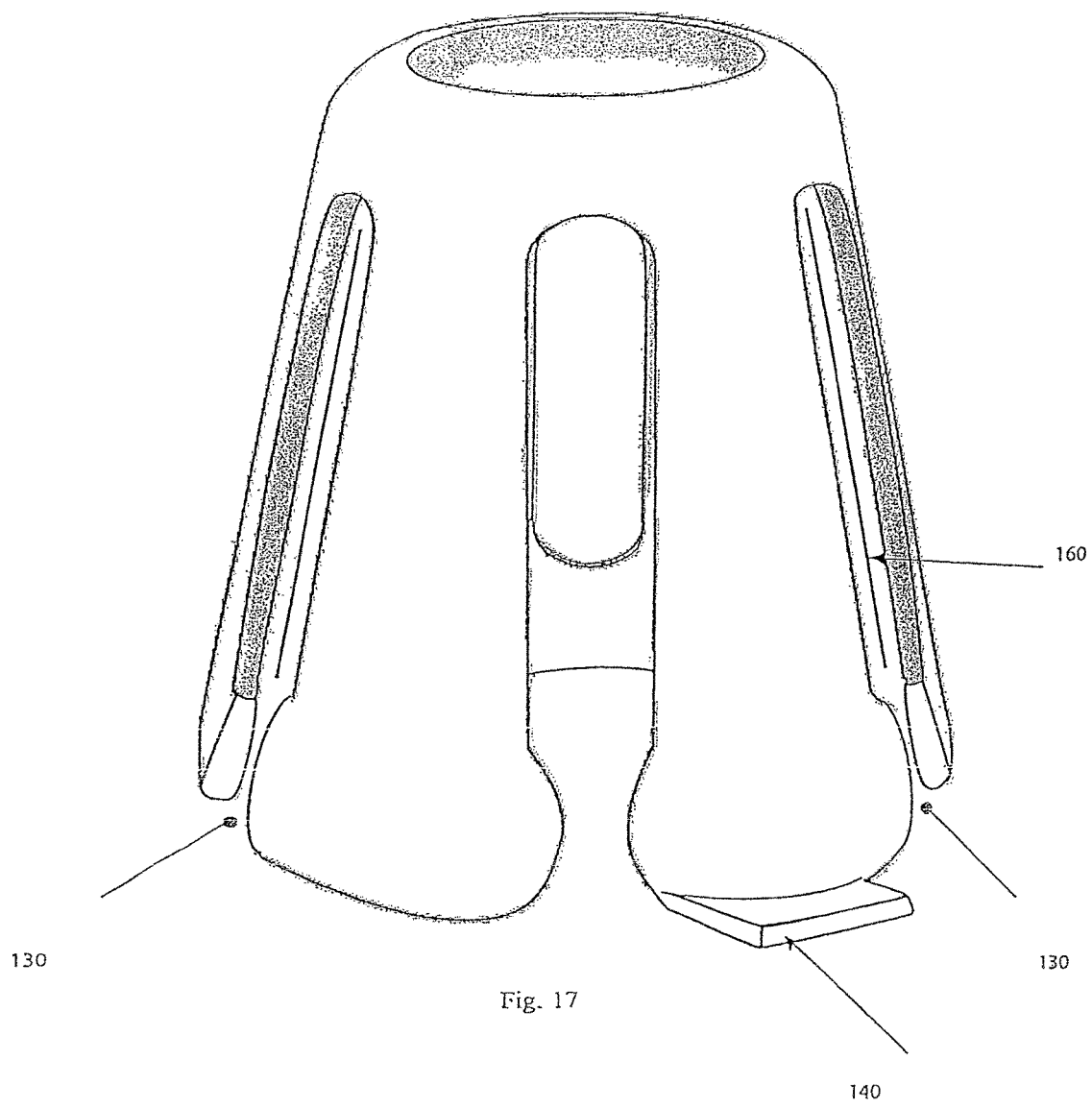

FIG. 17 depicts an embodiment of a device having more then one break 130 in the first end of the wall. Any desired number of breaks may be provided in the first end. FIG. 17 also shows grooves or ribs 160, which may be thinned or thickened portions of the wall, respectively. Ribs may also be strips of material (such as metal or plastic) attached to or embedded in the wall.

Figure 18:
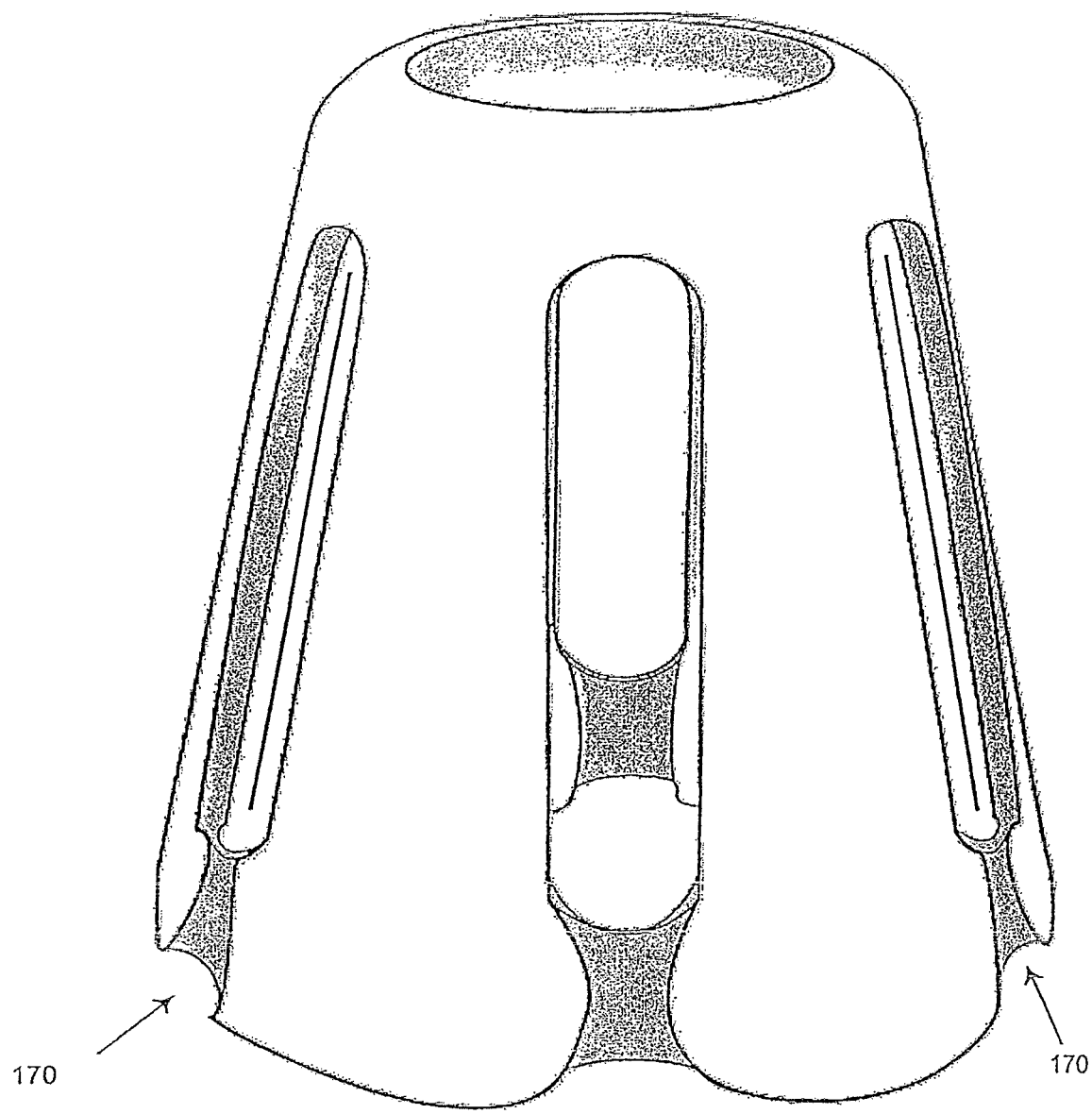

FIG. 18 depicts an embodiment of a device in which the first end has one or more thinned or webbed portions 170. Like the breaks described previously, the thinned or webbed portions may provide the device with greater flexibility. The thinned or webbed portions may be a thinner portion of the same material as the device's wall or may be made of a different material that is either thinner than and/or is more flexible than, the material of the rest of the first end.

Figure 19:
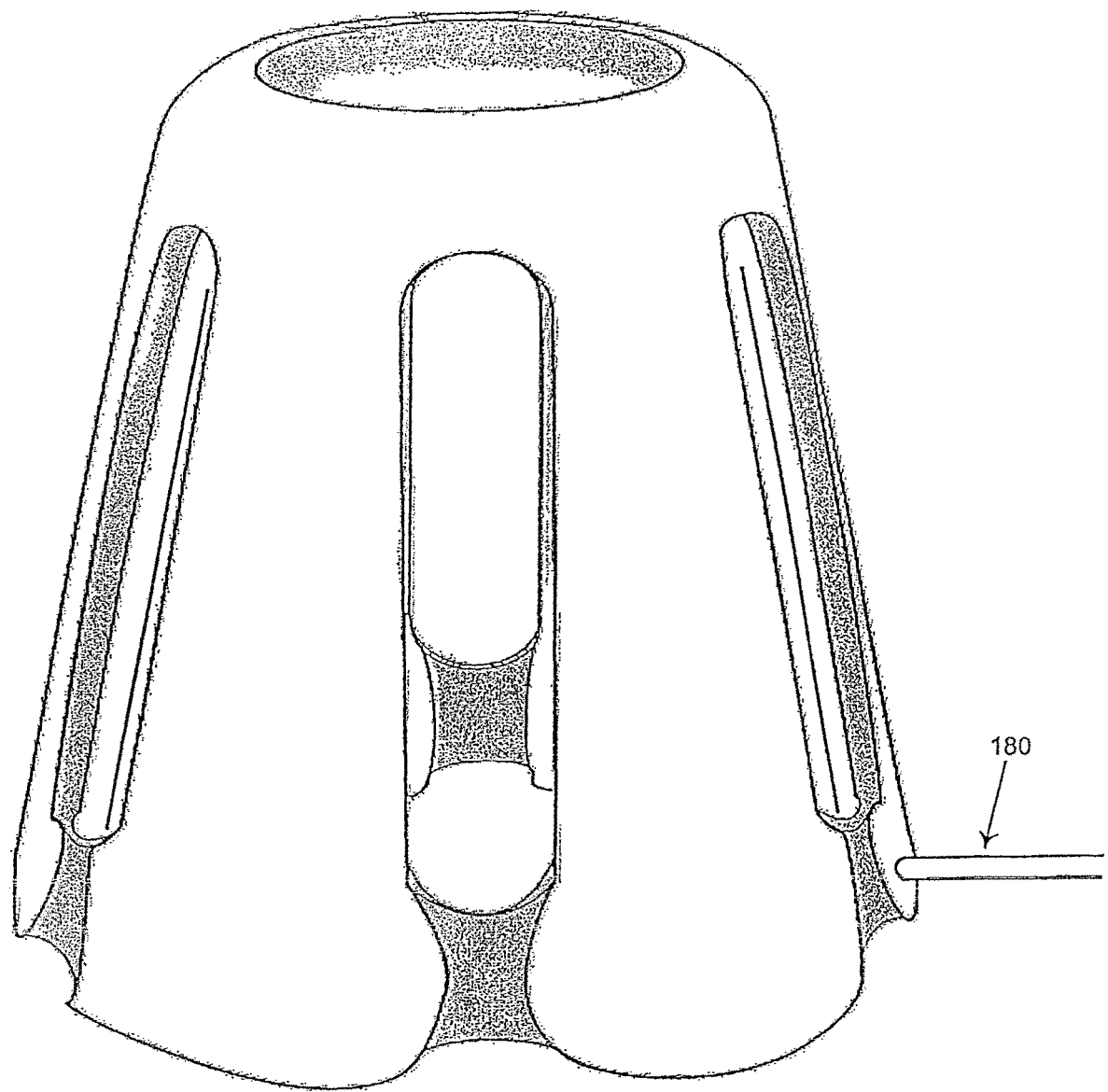

FIG. 19 depicts an embodiment of a device having attached to it a tether 180. The tether may be a pull string or other appendage to facilitate positioning and/or removal of the device. The tether may be a cannula, i.e., a tube that carries a fluid or gas, such as air, oxygen-enriched air, oxygen, etc.

Figure 20:
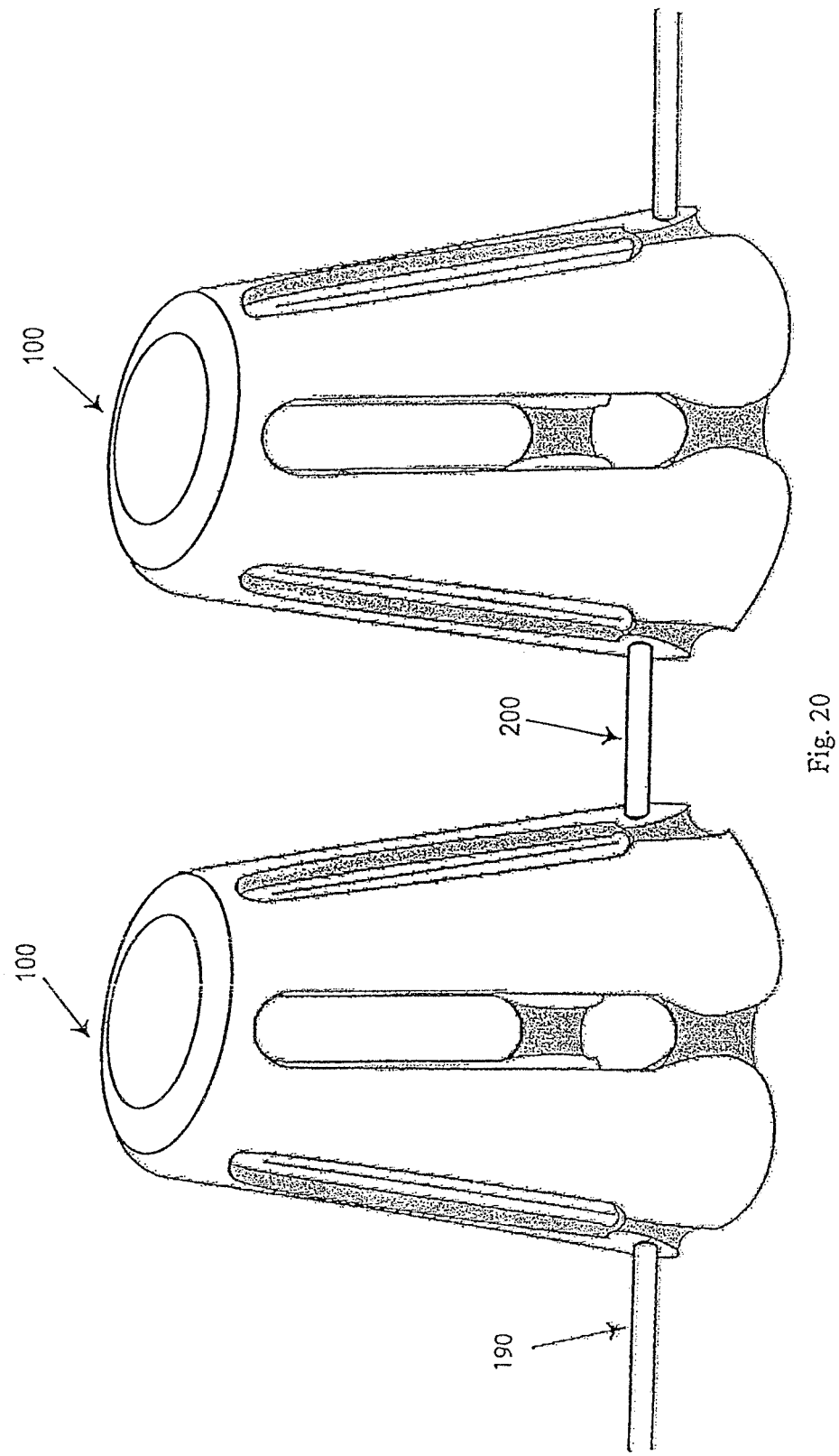

FIG. 20 shows devices 100 incorporated with a nasal cannula 190 for delivering gases such as air, oxygen, or oxygen-enriched air to a subject's nostrils. The devices depicted herein can also serve as adapters to receive more standard nasal cannula prongs to prevent them from contacting, irritating, eroding, or otherwise compromising nasal surfaces.

A connector 200 may connect devices 100. The connector may be rigid or pliable. It may be so shaped as to avoid contacting nasal tissue in order to prevent irritation or damage to the tissue. Alternatively, as shown in FIG. 21, there may be no connection between the devices; each device receives a cannula (or other tether).

As described earlier, devices may be given circular, elliptical, or other cross sections. This may be done to ensure that when a device is inserted into an anatomic space, such as a nostril, that space's geometry changes. The device may also be made of material sufficiently stiff to overcome the anatomic space's shape. In other words, the device may be intentionally designed not to conform the anatomy but to alter it. By changing the geometry, specifically, by increasing the anatomic space's volume, air flow through the space may be increased.

The devices disclosed herein can be used to aid in the administration of nasally supplied drugs, medications, herbal preparations, aromatherapy substances, homeopathic substances, and other substances, either at bedtime or during the day, for example, using a medication carrier inserted in the tubular element to deliver medications through the nose, or by coating, embedding, or integrally forming a device with the substance to be delivered. The nasal breathing assist device can also be used with other conventional devices to supply drugs and medications; for example, the user can insert the device into the nose, and spray a nasal medication, or moisture mist agent into the nose. The passageways in the device act to help circulate the medication or agent within the nasal passageways by keeping the nasal passages open.

Possible biologically active agents include without limitation, medicaments; vitamins; mineral supplements; substances used for the treatment, prevention, diagnosis, cure or mitigation of disease or illness; substances that affect the structure or function of the body; herbal preparations; aromatherapy substances; or homeopathic substances.

The therapeutic agents are used in amounts that are therapeutically effective, which varies widely depending largely on the particular agent being used. The amount of agent incorporated into the composition also depends upon the desired release profile, the concentration of the agent required for a biological effect, and the length of time that the biologically active substance has to be released for treatment. In certain embodiments, the biologically active substance may be blended with a polymer matrix at different loading levels, in one embodiment at room temperature and without the need for an organic solvent. In other embodiments, the compositions may be formulated as microspheres.

There is no critical upper limit on the amount of therapeutic agent incorporated except for that of an acceptable solution or dispersion viscosity to maintain the physical characteristics desired for the composition. The lower limit of the agent incorporated into the polymer system is dependent upon the activity of the drug and the length of time needed for treatment. Thus, the amount of the agent should not be so small that it fails to produce the desired physiological effect, nor so large that the agent is released in an uncontrollable manner. Typically, within these limits, amounts of the therapeutic agents from about 1% up to about 60% may be incorporated into the present delivery systems. However, lesser amounts may be used to achieve efficacious levels of treatment for agent that are particularly potent.

Specific types of biologically active agents include, either directly or after appropriate modification, without limitation: anti-angiogenesis factors, antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antiproliferatives; antimitotics; antimetabolite compounds; angiostatics; angiostatic steroids; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; catecholamines; diuretics; vasodilators including general coronary, peripheral and cerebral; central nervous system stimulants; cough and cold preparations, including decongestants; growth factors, hormones such as estradiol and other steroids, including corticosteroids; hypnotics; immunosuppressives; steroids; corticosteroids; glucocorticoids; muscle relaxants; parasympatholytics; psychostimulants; sedatives; and tranquilizers; and naturally derived or genetically engineered proteins, polysaccharides, glycoproteins, lipoproteins, interferons, cytokines, chemotherapeutic agents and other antineoplastics, antibiotics, anti-virals, anti-fungals, anti-inflammatories, anticoagulants, lymphokines, or antigenic materials.

To illustrate further, other types of biologically active agents that may be used, either directly or after appropriate modification, include peptide, proteins or other biopolymers, e.g., interferons, interleukins, tumor necrosis factor, nerve growth factor (NGF), brain-derived neurotrophic factor (BDNF), neurotrophin-3 (NT-3), neurotrophin-4/5 (NT-4/5), ciliary neurotrophic factor (CNTF), glial cell line-derived neurotrophic factor (GDNF), cholinergic differentiation factor/Leukemia inhibitory factor (CDF/LIF), epidermal growth factor (EGF), insulin-like growth factor (IGF), basic fibroblast growth factor (bFGF), platelet-derived growth factor (PDGF), erythropoietin, growth hormone, Substance-P, neurotensin, insulin, erythropoietin, albumin, transferrin, and other protein biological response modifiers.

Other examples of biologically active agents that may be used either directly or after appropriate modification include acebutolol, acetaminophen, acetohydoxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, betha nechol, biperiden, bisacodyl, bromocriptine, bromodiphenhydramine, brompheniramine, buclizine, bumetanide, busulfan, butabarbital, butaperazine, caffeine, calcium carbonate, captopril, carbamazepine, carbenicillin, carbidopa & levodopa, carbinoxamine inhibitors, carbonic anhydsase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, 6× chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colochicine, coloestipol, conjugated estrogen, contraceptives, cortisone, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetamine, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfiram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, ethchlorvynol, ethinyl estradiol, ethopropazine, ethosaximide, ethotoin, fenoprofen, ferrous fumarate, ferrous gluconate, ferrous sulfate, flavoxate, flecainide, fluphenazine, fluprednisolone, flurazepam, folic acid, furosemide, gemfibrozil, glipizide, glyburide, glycopyrrolate, gold compounds, griseofuwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, loperamide, lorazepam, magnesium hydroxide, magnesium sulfate, magnesium trisilicate, maprotiline, meclizine, meclofenamate, medroxyproyesterone, melenamic acid, melphalan, mephenytoin, mephobarbital, meprobamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulos, methyldopa, methylergonovine, methylphenidate, methylprednisolone, methysergide, metoclopramide, metolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystatin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin-v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl toloxamine, phenytoin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, psyllium, pyridostigmine, pyrodoxine, pyrilamine, pyrvinium, quinestrol, quinethazone, quinidine, quinine, ranitidine, rauwolfia alkaloids, riboflavin, rifampin, ritodrine, salicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocainide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B-12, vitamin C, vitamin D, vitamin E, vitamin K, xanthine, parathyroid hormone, enkephalins, and endorphins.

To illustrate further, antimetabolites may be used as upon appropriate modification if necessary, including without limitation methotrexate, 5-fluorouracil, cytosine arabinoside (ara-C), 5-azacytidine, 6-mercaptopurine, 6-thioguanine, and fludarabine phosphate. Antitumor antibiotics may include but are not limited to doxorubicin, daunorubicin, dactinomycin, bleomycin, mitomycin C, plicamycin, idarubicin, and mitoxantrone. *Vinca* alkaloids and epipodophyllotoxins may include, but are not limited to vincristine, vinblastine, vindesine, etoposide, and teniposide. Nitrosoureas, including carmustine, lomustine, semustine and streptozocin, may also be prodrugs, upon appropriate modification if necessary. Hormonal therapeutics may also be prodrugs, upon appropriate modification if necessary, such as corticosteriods (cortisone acetate, hydrocortisone, prednisone, prednisolone, methyl prednisolone dexamethasone, and fluocinolone acetonide), estrogens, (diethylstibesterol, estradiol, esterified estrogens, conjugated estrogen, chlorotiasnene), progestins (medroxyprogesterone acetate, hydroxy progesterone caproate, megestrol acetate), antiestrogens (tamoxifen), aromastase inhibitors (aminoglutethimide), androgens (testosterone propionate, methyltestosterone, fluoxymesterone, testolactone), antiandrogens (flutamide), LHRH analogues (leuprolide acetate), and endocrines for prostate cancer (ketoconazole). Antitumor drugs that are radiation enhancers may also be used as prodrugs, upon appropriate modification if necessary. Examples of such biologically active agents include, for example, the chemotherapeutic agents 5'-fluorouracil, mitomycin, cisplatin and its derivatives, taxol, bleomycins, daunomycins, and methamycins. Antibiotics may be used as prodrugs as well, upon appropriate modification if necessary, and they are well known to those of skill in the art, and include, for example, penicillins, cephalosporins, tetracyclines, ampicillin, aureothicin, bacitracin, chloramphenicol, cycloserine, erythromycin, gentamicin, gramacidins, kanamycins, neomycins, streptomycins, tobramycin, and vancomycin.

Other agents, upon appropriate modification if necessary, which may be used include those presently classified as investigational drugs, and can include, but are not limited to alkylating agents such as Nimustine AZQ, BZQ, cyclodisone, DADAG, CB10-227, CY233, DABIS maleate, EDMN, Fotemustine, Hepsulfam, Hexamethylmelamine, Mafosamide, MDMS, PCNU, Spiromustine, TA-077, TCNU and Temozolomide; antimetabolites, such as acivicin, Azacytidine, 5-aza-deoxycytidine, A-TDA, Benzylidene glucose, Carbetimer, CB3717, Deazaguanine mesylate, DODOX, Doxifluridine, DUP-785, 10-EDAM, Fazarabine, Fludarabine, MZPES, MMPR, PALA, PLAC, TCAR, TMQ, TNC-P and Piritrexim; antitumor antibodies, such as AMPAS, BWA770U, BWA773U, BWA502U, Amonafide, m-AMSA, CI-921, Datelliptium, Mitonafide, Piroxantrone, Aclarubicin, Cytorhodin, Epirubicin, esorubicin, Idarubicin, Iodo-doxorubicin, Marcellomycin, Morpholino anthracyclines, Pirarubicin, and SM-5887; microtubule spindle inhibitors, such as Amphethinile, Navelbine, and Taxol; the alkyl-lysophospholipids, such as BM41-440, ET-18-OCH3, and Hexacyclophosphocholine; metallic compounds, such as Gallium Nitrate, CL286558, CL287110, Cycloplatam, DWA2114R, NK121, Iproplatin, Oxaliplatin, Spiroplatin, Spirogermanium, and Titanium compounds; and novel compounds such as, for example, Aphidoicolin glycinate, Ambazone, BSO, Caracemide, DSG, Didemnin, B, DMFO, Elsamicin, Espertatrucin, Flavone acetic acid, HMBA, HHT, ICRF-187, Iododeoxyuridine, Ipomeanol, Liblomycin, Lonidamine, LY186641, MAP, MTQ, Merabarone SK&F104864, Suramin, Tallysomycin, Teniposide, THU and WR2721; and Toremifene, Trilosane, and zindoxifene.

In certain aspects, controlled-release compositions, upon contact with a mucous membrane or secretions therefrom, release a therapeutic substance over a sustained or extended period (as compared to the release from an isotonic saline solution). Such a system may result in prolonged delivery (over, for example, 2 to 4,000 hours, even 4 to 1500 hours) of effective amounts (e.g., 0.00001 mg/kg/hour to 10 mg/kg/hour) of the drug. This dosage form may be administered as is necessary depending on the subject being treated, the severity of the affliction, the judgment of the prescribing physician, and the like.

For treatment of diseases or conditions by drug delivery through the nasaopharyngeal mucous membrane, controlled-release compositions are adapted for transmucosal administration. As used herein, the term "anatomic area" refers to an area of nasal or nasopharyngeal anatomy. In certain embodiments, the pharmaceutical compositions are understood to exert their effect in part by contact with a portion of the anatomic area being treated. Contact refers to a physical touching, either directly with the subject composition being applied without intervening barrier to the anatomic area being treated, or indirectly, where the subject composition is applied to or is formed on a surface of an interposed material, passing through to come into direct contact with the anatomic area being treated. Contact, as used herein, includes those situations where the pharmaceutical compounds are initially positioned to contact the anatomic area being treated, and those situations where the controlled-release compositions are initially positioned in proximity to the anatomic area being treated without contacting it, and subsequently move, migrate, flow, spread, or are transported to enter into contact with the anatomic area being treated.

Contact may include partial contacts, wherein the pharmaceutical compounds only contact a portion of the anatomic area being treated, or the edge or periphery or margin of the anatomic area being treated. Contact of the pharmaceutical compounds with the anatomic area being treated occurs from a local rather than systemic administration of said compounds, as these terms are defined hereinafter. The composition may be formed as a flowable material, insertable into the anatomic area. A variety of devices and methods for inserting the composition into the preselected anatomic area will be familiar to practitioners of ordinary skill in the art, for example infusion, injection, topical application, spraying, painting, coating, formed gel placement, and others. The composition, alternatively, may be formed as a solid object implantable in the anatomic area, or as a film or mesh that may be used to cover a segment of the area. A variety of techniques for implanting solid objects in relevant anatomic areas will be likewise familiar to practitioners of ordinary skill in the art.

Some examples of sustained release devices and compositions are described in U.S. Pat. Nos. 5,618,563, 5,792,753, 5,942,241, 5,985,850, 6,096,728, 6,214,387, 6,217,911, 6,248,345, 6,335,035, 6,346,519, 6,426,339, 6,428,804, 6,451,335, 6,511,958, 6,514,514, 6,514,516, 6,521,259, 6,524,606, 6,524,607, 6,527,760, 6,528,097, 6,528,107, 6,534,081, 6,565,534, 6,582,715, 6,590,059, and 6,699,471; and in U.S. Patent Application Publication Nos. US 2003/0139811 A1 and US 2003/0093157 A1; and in PCT Publication No. WO/0061152 A1. All of these documents are hereby incorporated herein by this reference.

In some embodiments, the polymer composition may be a flexible or flowable material. When the polymer used is itself flowable, the polymer composition, even when viscous, need not include a biocompatible solvent to be flowable, although trace or residual amounts of biocompatible solvents may still be present.

In certain embodiments, a fluid polymer may be especially suitable for the transmucosal delivery of therapeutics. A fluid material may be adapted for injection or instillation into a tissue mass or into an actual or potential space. Certain types of fluid polymers may be termed flowable. A flowable material, often capable of assuming the shape of the contours of an irregular space, may be delivered to a portion of an actual or potential space to flow therefrom into a larger portion of the space. In this way, the flowable material may come to coat an entire post-operative surgical site after being inserted through an edge of an incision or after being instilled through a drain or catheter left in the surgical bed. Alternatively, if the flowable material is inserted under pressure through a device such as a needle or a catheter, it may perform hydrodissection, thus opening up a potential space and simultaneously coating the space with polymer. Such potential spaces suitable for hydrodissection may be found in various identifiable anatomic areas in the nose or nasopharynx. A flowable polymer may be particularly adapted for instillation through a needle, catheter or other delivery device such as an endoscope, since its flowable characteristics allow it to reach surfaces that extend beyond the immediate reach of the delivery device. A flowable polymer in a highly fluid state may be suitable for injection through needles or catheters into tissue masses, such as tumors or margins of resection sites. Physical properties of polymers may be adjusted to achieve a desirable state of fluidity or flowability by modification of their chemical components and crosslinking, using methods familiar to practitioners of ordinary skill in the art.

A flexible polymer may be used in the fabrication of a solid article. Flexibility involves having the capacity to be repeatedly bent and restored to its original shape. Solid articles made from flexible polymers are adapted for placement in anatomic areas where they will encounter the motion of adjacent organs or body walls. Certain areas of motion are familiar to practitioners dealing with nasal or nasopharyngeal problems. A flexible solid article can thus be sufficiently deformed by those moving tissues that it does not cause tissue damage. Flexibility is particularly advantageous where a solid article might be dislodged from its original position and thereby encounter an unanticipated moving structure; flexibility may allow the solid article to bend out of the way of the moving structure instead of injuring it. Solid articles may be formed as films, meshes, sheets, tubes, or any other shape appropriate to the dimensions and functional requirements of the particular anatomic area. Physical properties of polymers may be adjusted to attain a desirable degree of flexibility by modification of the chemical components and crosslinking thereof, using methods familiar to practitioners of ordinary skill in the art.

While it is possible that the biocompatible polymer or the biologically active agent may be dissolved in a small quantity of a solvent that is non-toxic to more efficiently produce an amorphous, monolithic distribution or a fine dispersion of the biologically active agent in the flexible or flowable composition, it is an advantage that, in an embodiment, no solvent is needed to form a flowable composition. Moreover, the use of solvents may be avoided because, once a polymer composition containing solvent is placed totally or partially within the body, the solvent dissipates or diffuses away from the polymer and must be processed and eliminated by the body, placing an extra burden on the body's clearance ability at a time when the illness (and/or other treatments for the illness) may have already deleteriously affected it.

However, when a solvent is used to facilitate mixing or to maintain the flowability of the polymer composition, it should be non-toxic, otherwise biocompatible, and should be used in relatively small amounts. Solvents that are toxic clearly should not be used in any material to be placed even partially within a living body. Such a solvent also must not cause substantial tissue irritation or necrosis at the site of administration.

Examples of suitable biocompatible solvents, when used, include N-methyl-2-pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, dimethyl-sulfoxide, oleic acid, or 1-dodecylazacycloheptan-2-one. In one embodiment, solvents include N-methyl-2-pyrrolidone, 2-pyrrolidone, dimethyl sulfoxide, and acetone because of their solvating ability and their biocompatibility.

The microspheres may be manufactured by incorporating the drug into the polymer matrix by either dissolving or suspending the drug into polymer solution and the mixture will be subsequently dried by techniques familiar to those skill in the arts to form microspheres. These techniques include but not limited to spray drying, coating, various emulsion methods and supercritical fluid processing. The microspheres may be mixed with a pharmaceutically acceptable diluent prior to the administration for injection. They may also be directly applied to the desired site, such as a surgical wound or cavity, by various delivery systems including pouring and spraying. The microspheres may also be mixed with pharmaceutically acceptable ingredients to create ointment or cream for topical applications.

In certain embodiments, the subject polymers are soluble in one or more common organic solvents for ease of fabrication and processing. Common organic solvents include such solvents as chloroform, dichloromethane, dichloroethane, 2-butanone, butyl acetate, ethyl butyrate, acetone, ethyl acetate, dimethylacetamide, N-methyl pyrrolidone, dimethylformamide, and dimethylsulfoxide.

In addition, the polymer compositions may comprise blends of the polymer with other biocompatible polymers or copolymers, so long as the additional polymers or copolymers do not interfere undesirably with the biocompatible, biodegradable and/or mechanical characteristics of the composition. Blends of the polymer with such other polymers may offer even greater flexibility in designing the precise release profile desired for targeted drug delivery or the precise rate of biodegradability desired. Examples of such additional biocompatible polymers include other poly(phosphoesters), poly(carbonates), poly(esters), poly(orthoesters), poly(amides), poly(urethanes), poly(imino-carbonates), and poly(anhydrides).

Pharmaceutically acceptable polymeric carriers may also comprise a wide range of additional materials. Without being limited thereto, such materials may include diluents, binders and adhesives, lubricants, disintegrants, colorants, bulking agents, flavorings, sweeteners, and miscellaneous materials such as buffers and adsorbents, in order to prepare a particular medicated composition, with the condition that none of these additional materials will interfere with the intended purpose of the subject composition.

Plasticizers and stabilizing agents known in the art may be incorporated in polymers. In certain embodiments, additives such as plasticizers and stabilizing agents are selected for their biocompatibility.

A composition may further contain one or more adjuvant substances, such as fillers, thickening agents or the like. In other embodiments, materials that serve as adjuvants may be associated with the polymer matrix. Such additional materials may affect the characteristics of the polymer matrix that results. For example, fillers, such as bovine serum albumin (BSA) or mouse serum albumin (MSA), may be associated with the polymer matrix. In certain embodiments, the amount of filler may range from about 0.1 to about 50% or more by weight of the polymer matrix, or about 2.5, 5, 10, 25, 40 percent. Incorporation of such fillers may affect the biodegradation of the polymeric material and/or the sustained release rate of any encapsulated substance. Other fillers known to those of skill in the art, such as carbohydrates, sugars, starches, saccharides, celluoses and polysaccharides, including mannitose and sucrose, may be used in certain embodiments.

In other embodiments, spheronization enhancers facilitate the production of subject polymeric matrices that are generally spherical in shape. Substances such as zein, microcrystalline cellulose or microcrystalline cellulose co-processed with sodium carboxymethyl cellulose may confer plasticity to the subject compositions as well as implant strength and integrity. In particular embodiments, during spheronization, extrudates that are rigid, but not plastic, result in the formation of dumbbell shaped implants and/or a high proportion of fines, and extrudates that are plastic, but not rigid, tend to agglomerate and form excessively large implants. In such embodiments, a balance between rigidity and plasticity is desirable. The percent of spheronization enhancer in a formulation depends on the other excipient characteristics and is typically in the range of 10-90% (w/w).

Buffers, acids and bases may be incorporated in the subject compositions to adjust their pH. Agents to increase the diffusion distance of agents released from the polymer matrix may also be included.

Disintegrants are substances which, in the presence of liquid, promote the disruption of the subject compositions. Disintegrants are most often used in implants, in which the function of the disintegrant is to counteract or neutralize the effect of any binding materials used in the subject formulation. In general, the mechanism of disintegration involves moisture absorption and swelling by an insoluble material. Examples of disintegrants include croscarmellose sodium and crospovidone that, in certain embodiments, may be incorporated into the polymeric matrices in the range of about 1-20% of total matrix weight. In other cases, soluble fillers such as sugars (mannitol and lactose) may also be added to facilitate disintegration of the subject compositions upon use.

Other materials may be used to advantage to control the desired release rate of a therapeutic agent for a particular treatment protocol. For example, if the sustained release is too slow for a particular application, a pore-forming agent may be added to generate additional pores in the matrix. Any biocompatible water-soluble material may be used as the pore-forming agent. They may be capable of dissolving, diffusing or dispersing out of the formed polymer system whereupon pores and microporous channels are generated in the system. The amount of pore-forming agent (and size of dispersed particles of such pore-forming agent, if appropriate) within the composition should affect the size and number of the pores in the polymer system.

Pore-forming agents include any pharmaceutically acceptable organic or inorganic substance that is substantially miscible in water and body fluids and will dissipate from the forming and formed matrix into aqueous medium or body fluids or water-immiscible substances that rapidly degrade to water-soluble substances. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The size and extent of the pores may be varied over a wide range by changing the molecular weight and percentage of pore-forming agent incorporated into the polymer system.

The charge, lipophilicity or hydrophilicity of any subject polymeric matrix may be modified by attaching in some fashion an appropriate compound to the surface of the matrix. For example, surfactants may be used to enhance wettability of poorly soluble or hydrophobic compositions. Examples of suitable surfactants include dextran, polysorbates and sodium lauryl sulfate. In general, surfactants are used in low concentrations, generally less than about 5%.

Binders are adhesive materials that may be incorporated in polymeric formulations to bind and maintain matrix integrity. Binders may be added as dry powder or as solution. Sugars and natural and synthetic polymers may act as binders. Materials added specifically as binders are generally included in the range of about 0.5%-15% w/w of the matrix formulation. Certain materials, such as microcrystalline cellulose, also used as a spheronization enhancer, also have additional binding properties.

Various coatings may be applied to modify the properties of the matrices. Three exemplary types of coatings are seal, gloss and enteric coatings. Other types of coatings having various dissolution or erosion properties may be used to further modify subject matrices behavior, and such coatings are readily known to one of ordinary skill in the art.

The seal coat may prevent excess moisture uptake by the matrices during the application of aqueous based enteric coatings. The gloss coat generally improves the handling of the finished matrices. Water-soluble materials such as hydroxypropyl cellulose may be used to seal coat and gloss coat implants. The seal coat and gloss coat are generally sprayed onto the matrices until an increase in weight between about 0.5% and about 5%, often about 1% for a seal coat and about 3% for a gloss coat, has been obtained.

Enteric coatings may include polymers which are insoluble in the low pH (less than 3.0) of the stomach, but are soluble in the elevated pH (greater than 4.0) of the small intestine. Polymers such as EUDRAGIT, RohmTech, Inc., Malden, Mass., and AQUATERIC, FMC Corp., Philadelphia, Pa., may be used and are layered as thin membranes onto the implants from aqueous solution or suspension or by a spray drying method. The enteric coat is generally sprayed to a weight increase of about one to about 30%, or about 10 to about 15% and may contain coating adjuvants such as plasticizers, surfactants, separating agents that reduce the tackiness of the implants during coating, and coating permeability adjusters.

The present compositions may additionally contain one or more optional additives such as fibrous reinforcement, colorants, perfumes, rubber modifiers, modifying agents, etc. In practice, each of these optional additives should be compatible with the resulting polymer and its intended use. Examples of suitable fibrous reinforcement include PGA microfibrils, collagen microfibrils, cellulosic microfibrils, and olefinic microfibrils. The amount of each of these optional additives employed in the composition is an amount necessary to achieve the desired effect.

The subject polymers may be formed in a variety of shapes. For example, in certain embodiments, subject polymer matrices may be presented in the form of microparticles or nanoparticles. Such particles may be prepared by a variety of methods known in the art, including for example, solvent evaporation, spray-drying or double emulsion methods.

The shape of microparticles and nanoparticles may be determined by scanning electron microscopy. Spherically shaped nanoparticles are used in certain embodiments for circulation through the bloodstream. If desired, the particles may be fabricated using known techniques into other shapes that are more useful for a specific application.

In addition to intracellular delivery of a therapeutic agent, it also possible that particles of the subject compositions, such as microparticles or nanoparticles, may undergo endocytosis, thereby obtaining access to the cell. The frequency of such an endocytosis process will likely depend on the size of any particle.

In certain embodiments, solid articles useful in defining shape and providing rigidity and structural strength to the polymeric matrices may be used. For example, a polymer may be formed on a mesh or other weave for implantation. A polymer may also be fabricated as a stent or as a shunt, adapted for holding open areas within body tissues or for draining fluid from one body cavity or body lumen into another. Further, a polymer may be fabricated as a drain or a tube suitable for removing fluid from a post-operative site, and in some embodiments adaptable for use with closed section drainage systems such as Jackson-Pratt drains and the like familiar in the art.

The mechanical properties of the polymer may be important for the processability of making molded or pressed articles for implantation. For example, the glass transition temperature may vary widely but must be sufficiently lower than the temperature of decomposition to accommodate conventional fabrication techniques, such as compression molding, extrusion or injection molding.

In certain embodiments, the polymers and blends, upon contact with body fluids, undergo gradual degradation. The life of a biodegradable polymer in vivo depends, among other things, upon its molecular weight, crystallinity, biostability, and the degree of crosslinking. In general, the greater the molecular weight, the higher the degree of crystallinity, and the greater the biostability, the slower biodegradation will be.

If a subject polymer matrix is formulated with a therapeutic agent, release of such an agent for a sustained or extended period as compared to the release from an isotonic saline solution generally results. Such release profile may result in prolonged delivery (over, say 1 to about 4,000 hours, or alternatively about 4 to about 1500 hours) of effective amounts (e.g., about 0.00001 mg/kg/hour to about 10 mg/kg/hour) of the agent associated with the polymer.

A variety of factors may affect the desired rate of hydrolysis of polymers, the desired softness and flexibility of the resulting solid matrix, rate and extent of bioactive material release. Some of such factors include: the selection of the various substituent groups, such as the phosphate group making up the linkage in the polymer backbone (or analogs thereof), the enantiomeric or diastereomeric purity of the monomeric subunits, homogeneity of subunits found in the polymer, and the length of the polymer. For instance, the present disclosure contemplates heteropolymers with varying linkages, and/or the inclusion of other monomeric elements in the polymer, in order to control, for example, the rate of biodegradation of the matrix.

To illustrate further, a wide range of degradation rates may be obtained by adjusting the hydrophobicities of the backbones or side chains of the polymers while still maintaining sufficient biodegradability for the use intended for any such polymer. Such a result may be achieved by varying the various functional groups of the polymer. For example, the combination of a hydrophobic backbone and a hydrophilic linkage produces heterogeneous degradation because cleavage is encouraged whereas water penetration is resisted. In another example, it is expected that use of substituent on phosphate in the polymers that is lipophilic, hydrophobic or bulky group would slow the rate of degradation. For example, it is expected that conversion of the phosphate side chain to a more lipophilic, more hydrophobic or more sterically bulky group would slow down the rate of biodegradation. Thus, release is usually faster from polymer compositions with a small aliphatic group side chain than with a bulky aromatic side chain.

One protocol generally accepted in the field that may be used to determine the release rate of any therapeutic agent or other material loaded in the polymer matrices involves degradation of any such matrix in a 0.1 M PBS solution (pH 7.4) at 37° C., an assay known in the art. For purposes of the present disclosure, the term "PBS protocol" is used herein to refer to such protocol.

In certain instances, the release rates of different polymer systems may be compared by subjecting them to such a protocol. In certain instances, it may be necessary to process polymeric systems in the same fashion to allow direct and relatively accurate comparisons of different systems to be made. Such comparisons may indicate that any one polymeric system releases incorporated material at a rate from about 2 or less to about 1000 or more times faster than another polymeric system. Alternatively, a comparison may reveal a rate difference of about 3, 5, 7, 10, 25, 50, 100, 250, 500 or 750. Even higher rate differences are contemplated by the present disclosure and release rate protocols.

In certain embodiments, when formulated in a certain manner, the release rate for polymer systems may present as mono- or bi-phasic. Release of any material incorporated into the polymer matrix, which is often provided as a microsphere, may be characterized in certain instances by an initial increased release rate, which may release from about 5 to about 50% or more of any incorporated material, or alternatively about 10, 15, 20, 25, 30 or 40%, followed by a release rate of lesser magnitude.

The release rate of any incorporated material may also be characterized by the amount of such material released per day per mg of polymer matrix. For example, in certain embodiments, the release rate may vary from about 1 ng or less of any incorporated material per day per mg of polymeric system to about 5000 or more ng/day·mg. Alternatively, the release rate may be about 10, 25, 50, 75, 100, 125, 150, 175, 200, 250, 300, 350, 400, 450, 500, 600, 700, 800 or 900 ng/day·mg. In still other embodiments, the release rate of any incorporated material may be 10,000 ng/day·mg or even higher. In certain instances, materials incorporated and characterized by such release rate protocols may include therapeutic agents, fillers, and other substances.

In another aspect, the rate of release of any material from any polymer matrix may be presented as the half-life of such material in the such matrix.

In addition to the embodiment involving protocols for in vitro determination of release rates, in vivo protocols, whereby in certain instances release rates for polymeric systems may be determined in vivo, are also contemplated by the present disclosure. Other assays useful for determining the release of any material from the polymers of the present system are known in the art.

In some embodiments, for delivery of a therapeutic agent, the agent is added to the polymer composition. A variety of methods are known in the art for encapsulating a biologically active substance in a polymer. For example, the agent or substance may be dissolved to form a homogeneous solution of reasonably constant concentration in the polymer composition, or it may be dispersed to form a suspension or dispersion within the polymer composition at a desired level of "loading" (grams of biologically active substance per grams of total composition including the biologically active substance, usually expressed as a percentage).

In part, a polymer composition useful in the treatment of pain, inflammation, infection, or other problems, includes both: (a) a therapeutic agent, and (b) a biocompatible and optionally biodegradable polymer, such as one having the recurring monomeric units shown in one of the foregoing formulas, or any other biocompatible polymer mentioned above or known in the art. In certain embodiments in which the subject composition will be used to treat pain, the agent is an analgesic or anesthetic; for inflammation, a steroidal or non-steroidal antiinflammatory agent; and for infection, an antimicrobial effective against the pathogen(s) of concern, such as an antibiotic, antifungal, antimycotic, antimalarial, antimycobacterial, antiparasitic, or antiviral. In some embodiments, the subject compositions encapsulate more than one agent for treatment of one or more problems.

In its simplest form, a delivery system for a transmucosal therapeutic agent consists of a dispersion of such an agent into one of the polymers described above. In other embodiments, an article is used for implantation, injection, or otherwise placed totally or partially within the body, the article comprising a therapeutic composition for transmucosal delivery. It may be particularly important that such an article result in minimal tissue irritation when applied to, implanted in or injected into vascularized tissue, hypovascularized tissue, post-operative tissue or tissue exposed to previous radiation that is part of the nose or nasopharynx. In certain embodiments, a solid, flowable or fluid article is inserted within an anatomic area by implantation, injection, endoscopy or otherwise being placed within the anatomic area of the subject being treated.

As a structural medical device, the polymer compositions provide a wide variety of physical forms having specific chemical, physical and mechanical properties suitable for insertion into an anatomic area.

Biocompatible delivery systems and articles thereof, may be prepared in a variety of ways known in the art. The subject polymer may be melt processed using conventional extrusion or injection molding techniques, or these products may be prepared by dissolving in an appropriate solvent, followed by formation of the device, and subsequent removal of the solvent by evaporation or extraction, e.g., by spray drying. By these methods, the polymers may be formed into articles of almost any size or shape desired, for example, implantable solid discs or wafers or injectable rods, microspheres, or other microparticles. Typical medical articles also include such as implants as laminates for degradable fabric or coatings to be placed on other implant devices.

Nasal devices may be provided with one or more therapeutic agents incorporated in gels, polymers, powders, and/or liquids that coat, are embedded in or through the device. The structure of the device itself may be formed in whole or in part by the drug formulation. The nasal device may dissolve in whole or in part with use or may be nondissolvable. A device may be inserted temporarily or permanently.

A therapeutic formulation may be selected so that inhalation causes dislodgment or vaporization of a therapeutic into the patient's airsteam for delivery deeper in the airway (for example, in the brachial tree and/or alveoli).

In one embodiment, certain polymer compositions may be used to form a soft, drug-delivery "depot" that can be administered as a liquid, for example, by injection, but which remains sufficiently viscous to maintain the drug within the localized area around the injection site. By using a polymer composition in flowable form, even the need to make an incision can be eliminated. In any event, the flexible or flowable delivery "depot" will adjust to the shape of the space it occupies within the body with a minimum of trauma to surrounding tissues.

When the polymer composition is flexible or flowable, it may be placed anywhere within the body, including into an anatomic area. It may be inserted into the anatomic area either through an open surgical wound, under direct or indirect vision, or through any of the access devices routinely used in the art to enter such areas, for example, indwelling or acutely-inserted catheters, needles, drains, superselective angiography means and the like. A flowable or fluid polymer may be adapted for mixing with the transudate or exudate found within or expected to gather within the anatomic area. A flowable or fluid polymer may be instilled in an anatomic area during surgery on organs or structures therein to decrease the likelihood of recurrent disease when there is a high risk for its development. In certain embodiments, a polymer composition may also be incorporated in access devices so that a therapeutic agent is released into the anatomic area within which the access device resides. The polymer composition may also be used to produce coatings for other solid implantable devices for treatment.

Once a system or implant article is in place, it should remain in at least partial contact with a biological fluid, such as blood, tissue fluid, lymph, or secretions from organ surfaces or mucous membranes, and the like to allow for sustained release of any encapsulated therapeutic agent, e.g., a therapeutic agent.

These examples of the clinical utility of the disclosed devices and methods have been provided for illustrative purposes only. Other exemplary utilizations will be apparent to practitioners of ordinary skill in the art using no more than routine experimentation.

The various nasal dilators, stents, and other devices may be combined with other forms of therapy to provide multimodality treatments. For example, a person with a nasal or upper airway disorder may be treated by any combination of a nasal device disclosed herein and a course of antibiotics (by any route of administration), nasal sprays, and/or nasal irrigators. Disorders that may especially amenable to such multi-modality treatment include upper airway allergies, congestion, rhinitis, and sinus infections.

The devices disclosed herein may also be used to reduce or eliminate nasal stenosis and/or scarring following nasal surgery such as septoplasty or rhinoplasty. A device or devices may be positioned in one or both nostrils following surgery to help hold the nostril in an opened structure. The device(s) can also prevent contact between surgical surface to prevent formation of adhesions or scar tissue. The device(s) may be employed temporarily or permanently. They may be positioned as a step of a surgical procedure or in an out-patient setting. They may be used as a preventive measure before any postsurgical signs or symptoms occur, or as a remedial measure after an abnormal healing shape, scarring, or adhesions are observed.

The invention may be embodied in other specific forms without departing from the spirit or essential characteristics thereof. The present embodiments are therefore to be considered illustrative and not restrictive, the scope of the invention being dictated by the appended claims rather than by the foregoing description, and all changes which come within the meaning and range of equivalency of the claims are therefore intended to be embraced therein.

We claim:

1. A pair of nasal inserts, each nasal insert comprising a wall in the shape of a frustroconical tube, the wall including a first end defining a first orifice and a second end defining a second orifice, and wherein:
    the first end has a diameter, diagonal measurement, or cross-sectional area larger than that of the second end;
    the first end further defines at least one break in the wall, so that the first end incompletely encircles the first orifice, the break increasing the flexibility of the first end;
    the second end completely encircles the second orifice; and further comprising:
    a flexible and resilient coupler element that connects to the first end of each nasal insert.

2. The nasal inserts of claim 1, wherein the wall defines at least one passageway transverse to a longitudinal axis of the tube.

3. The nasal inserts of claim 2, wherein the at least one passageway is continuous with the at least one break in the wall.

4. The nasal inserts of claim 1, further comprising a foot protruding from the first end of the wall.

5. The nasal inserts of claim 4, wherein the foot is so flexible as to permit selective positioning of the foot.

6. The nasal inserts of claim 5, wherein the foot comprises an embedded wire.

7. The nasal inserts of claim 1, further comprising a clip.

8. The nasal inserts of claim 1, wherein an inner surface of the tube defines at least one groove.

9. The nasal inserts of claim 1, further comprising a therapeutic agent.

10. The nasal inserts of claim 9, wherein the therapeutic agent is integrally formed with the device.

11. The nasal inserts of claim 9, wherein the therapeutic agent is coated on a surface of the device.

12. The nasal inserts of claim 9, wherein the therapeutic agent is provided with an insert attached to the device.

13. The nasal inserts of claim 12, wherein the insert is removably attached to the device.

14. The nasal inserts of claim 1, further comprising a filter so attached to the device as to span the tube.

15. The nasal inserts of claim 14, wherein the filter is attached to the device by a snap-fit.

16. The nasal inserts of claim 14, wherein the filter is attached to the device by hook-and-loop fasteners.

17. A device comprising the device of claim 1 attached to a nasal cannula.

18. A method of preventing postsurgical complications of nasal surgery comprising: inserting the device of claim 1 into nostrils of a subject after performing nasal surgery upon the subject.

* * * * *